US008143475B2

(12) United States Patent
Li

(10) Patent No.: US 8,143,475 B2
(45) Date of Patent: Mar. 27, 2012

(54) SOYBEAN PROMOTER LTP4 AND FLOWER-PREFERRED EXPRESSION THEREOF IN TRANSGENIC PLANTS

(75) Inventor: Zhongsen Li, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 457 days.

(21) Appl. No.: 12/332,447

(22) Filed: Dec. 11, 2008

(65) Prior Publication Data

US 2009/0158464 A1 Jun. 18, 2009

Related U.S. Application Data

(60) Provisional application No. 61/014,567, filed on Dec. 18, 2007.

(51) Int. Cl.
| | |
|---|---|
| *A01H 1/00* | (2006.01) |
| *A01H 5/00* | (2006.01) |
| *A01H 5/02* | (2006.01) |
| *C07H 21/04* | (2006.01) |
| *C12N 15/82* | (2006.01) |
| *C12N 5/04* | (2006.01) |

(52) U.S. Cl. ........ 800/278; 800/287; 800/295; 800/298; 800/323; 800/323.2; 800/323.3; 536/24.1; 435/468; 435/419; 435/320.1

(58) Field of Classification Search .......................... None
See application file for complete search history.

(56) References Cited

U.S. PATENT DOCUMENTS

2008/0034453 A1* 2/2008 Cheikh et al. ................. 800/294

OTHER PUBLICATIONS

Shoemaker et al. Accession No. BG352390, Database EST, Jul. 22, 2004.*
Bustos et al, The EMBO Journal,1991, vol. 10, pp. 1469-1479.*
Benfey et al, 1990, Science 250:959-966.*
Kim et al, 1994, Plant Mol. Biol. 24:105-117.*
Chen et al (2000, Sex. Plant Reprod. 13:85-94.*
Federico et al. The Complex Developmental Expression of a Novel Stress-Responsive Barley Ltp Gene is Determined by a Shortened Promoter Sequence. Plant Molecular Biology, vol. 57, p. 35-51, 2005.
Yubero-Serrano et al. Identification of a Strawberry Encoding a Non-Specific Lipid Transfer Protein that Responds to ABA, Wounding and Cold Stress. Gene Journal of Express Botany, vol. 54, p. 1865-1877, 2003.
Thoma et al. Tissue-Specific Expression of a Gene Encoding a Cell Wall-Localized Lipid Transfer Protein from *Arabidopsis*. Plant Physiology, vol. 105, p. 35-45, 1994.
Sabala et al. Tissue-Specific Expression of Pa18, a Putative Lipid Transfer Protein Gene, during Embryo Development in Norway Spruce (*Picea abies*). Plant Molecular Biology, vol. 42, p. 461-478, 2000.
Vignols et al. Characterization of a Rice Gene Coding for a Lipid Transfer Protein. Gene, vol. 142, p. 265-270, 1994.
Toonen et al. AtLTP1 Luciferase Expression During Carrot Somatic Embryogenesis. The Plant Journal, vol. 12, p. 1213-1221, 1997.
Sohal et al. Plant Molecular Biology, vol. 41, p. 75-87, 1999.
Pelese-Siebenbourg et al. Gene, vol. 148, p. 305-308, 1994.
Kader, Jean-Claude. Annual Review of Plant Physiology and Plant Molecular Biology, vol. 47, p. 627-654, 1996.
George et al. Genome, vol. 50, p. 470-478, 2007.
Jaillon et al. Nature, vol. 449, p. 463-467, 2007.
Finkina et al. Biokhimiia (Biochemistry), vol. 72, p. 430-438, 2007.
Chandler, et al., "Two Regulatory Genes of the Maize Anthocyanin Pathway Are Homologous: Isolation . . . ", The Plant Cell, vol. 1, pp. 1175-1183, Dec. 1989.
Chang, et al., "Overproduction of Cytokinins in Petunia Flowers Transformed with PSAG12-IPT Delays . . . ", Plant Physiology, vol. 132, pp. 2174-2183, Aug. 2003.
Ebert, et al., "Identification Of An Essential Upstream Element In The Nopaline Synthase Promoter By Stable . . . ", Proc. Natl. Acad. Sci., vol. 84, pp. 5745-5749, Aug. 1987.
Kakimoto, "Biosynthesis of Cytokinins", J. Plant Res., vol. 116, pp. 233-239, 2003.
Lawton, et al., "Expression of a Soybean B-conclycinin Gene Under the Control of the Cauliflower Mosaic Virus . . . ", Plant Molecular Biol., vol. 9, pp. 315-324, 1987.
Matz, et al., "Fluorescent Proteins from Nonbioluminescent Anthozoa Species", Nature Biotechnology, vol. 17, pp. 969-973, 1999.
Mori, et al., "Heterologous Expression of the Flavonoid 3',5'-Hydroxylase Gene of Vinca Major Alters Flower . . . ", Plant Cell Rep, vol. 22, pp. 415-421, 2004.
Odell, et al., "Identification of DNA Sequences Required for Activity of the Cauliflower Mosaic . . . ", Nature, vol. 313, pp. 810-812, Feb. 1985.
Okamuro, et al., "Regulation of Plant Gene Expression: General Principles", The Biochemistry of Plants, vol. 15, pp. 1-82, 1989.
Pellegrineschi, et al., "Expression of Horseradish Peroxidase in Transgenic Tobacco", Biochemical Society Transitions, vol. 23, pp. 247-250, 1995.
Sanger, et al., "Characteristics of a Strong Promoter from Figwort Mosaic Virus: Comparison.with the Analogous . . . ", Plant Molecular Biol., vol. 14, pp. 433-443, 1990.
Tanaka, et al., "Genetic Engineering in Floriculture", Plant Cell, Tissue and Organ Culture, vol. 80, pp. 1-24, 2005.
Walker, et al., "DNA Sequences Required for Anaerobic Expression of the Maize Alcohol . . . ", Proc. Natl. Acad. Sci. USA, vol. 84, pp. 6624-6628, Oct. 1987.
Yang, et al., "Maize Sucrose Synthase-1 Promoter Directs Phloem Cell-specific Expression of Gus Gene . . . ", Proc. Natl. Acad. Sci. USA, vol. 87, pp. 4144-4148, Jun. 1990.
Young, et al., "Senescence-induced Expression of Cytokinin Reverses Pistil Abortion During Maize Flower Development", The Plant Journal, vol. 38, pp. 910-922, 2004.

* cited by examiner

*Primary Examiner* — Eileen B O Hara

(57) ABSTRACT

The promoter of a soybean lipid transfer protein LTP4 and fragments thereof and their use in promoting the expression of one or more heterologous nucleic acid fragments in plants are described.

17 Claims, 4 Drawing Sheets

US 8,143,475 B2

Figure 1:
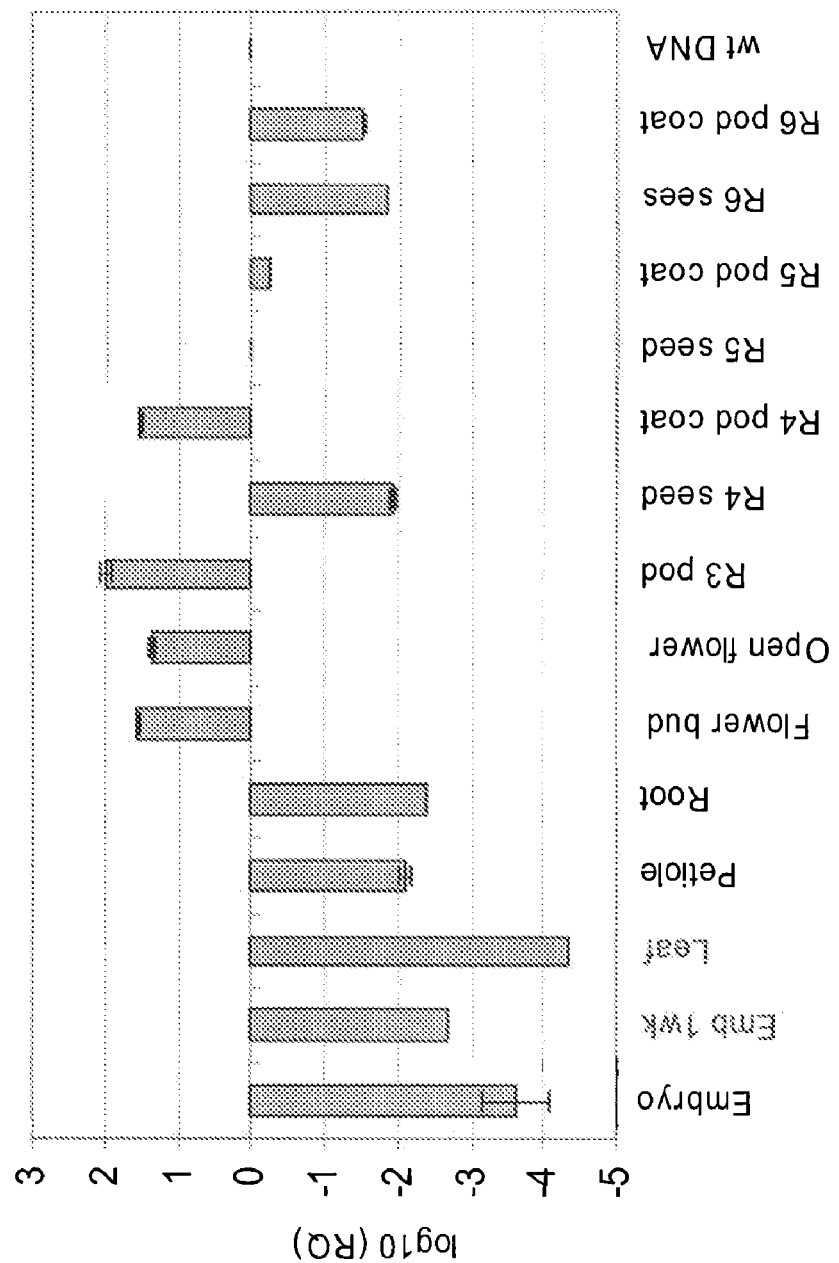

SEQUENCE LISTING

```
<160> NUMBER OF SEQ ID NOS: 33

<210> SEQ ID NO 1
<211> LENGTH: 508
<212> TYPE: DNA
<213> ORGANISM: Glycine max

<400> SEQUENCE: 1
gggctggtac tcaatgtgac aaaagagaga taatgacaaa tataatgtat aagtgagatg      60
tttaaaagat cactactctc gaaataaaat tcagtctaat tcaatctagc ccaaatggac     120
tagataaagc aactcaattt gacaactcta gccgtgctaa ccaagaattg gcaattacaa     180
aatatccaaa attgaaacca ttttgatata caaattaaag aaatccgtgc aataaagtgg     240
cctacactac aacaagaaag cagaagaaga ggtaacgaag tcgcaagtgg ttgcatgtaa     300
tgtaagtaac accggcctat agctcaccca ccaatataat aaacccccat caattttcat     360
aaattcatct aacgtcgcca ctcatttcca atctatccac tcatctatat aaacaccaca     420
ctacatcact tgttctcacc acattccaaa acacaaacac atacattgta gtatcacttt     480
tgtctcggaa tttgttcttt tgagttcc                                       508

<210> SEQ ID NO 2
<211> LENGTH: 17
<212> TYPE: DNA
<213> ORGANISM: Artificial sequence
<220> FEATURE:
<223> OTHER INFORMATION: MPSS TAG

<400> SEQUENCE: 2
gatccaccaa ctgcgac                                                    17

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
```

-continued

```
tggcatcaac gacgaatacg                                              20

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
tgcaatgtca gcgtcccttc                                              20

<210> SEQ ID NO 5
<211> LENGTH: 24
<212> TYPE: DNA
<213> ORGANISM: Artificial sequence
<220> FEATURE:
<223> OTHER INFORMATION: primer

<400> SEQUENCE: 5
catgattggg agaaaccttc agct                                         24

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
agattgggcc agaggatcct                                              20

<210> SEQ ID NO 7
<211> LENGTH: 26
<212> TYPE: DNA
<213> ORGANISM: Artificial sequence
<220> FEATURE:
<223> OTHER INFORMATION: primer

<400> SEQUENCE: 7
gaccaagaca cactcgttca tatatc                                       26

<210> SEQ ID NO 8
<211> LENGTH: 25
<212> TYPE: DNA
<213> ORGANISM: Artificial sequence
<220> FEATURE:
<223> OTHER INFORMATION: primer

<400> SEQUENCE: 8
tctgctgctc aatgtttaca aggac                                        25

<210> SEQ ID NO 9
<211> LENGTH: 48
<212> TYPE: DNA
<213> ORGANISM: Artificial sequence
<220> FEATURE:
<223> OTHER INFORMATION: adaptor

<400> SEQUENCE: 9
gtaatacgac tcactatagg gcacgcgtgg tcgacggccc gggctggt               48

<210> SEQ ID NO 10
<211> LENGTH: 26
<212> TYPE: DNA
<213> ORGANISM: Artificial sequence
<220> FEATURE:
```

<223> OTHER INFORMATION: primer

<400> SEQUENCE: 10
caaaaccaca catgcaacct ttaagc     26

<210> SEQ ID NO 11
<211> LENGTH: 25
<212> TYPE: DNA
<213> ORGANISM: Artificial sequence
<220> FEATURE:
<223> OTHER INFORMATION: primer

<400> SEQUENCE: 11
gtaatacgac tcactatagg gcacg     25

<210> SEQ ID NO 12
<211> LENGTH: 32
<212> TYPE: DNA
<213> ORGANISM: Artificial sequence
<220> FEATURE:
<223> OTHER INFORMATION: primer

<400> SEQUENCE: 12
ccatggaact caaaagaaca aattccgaga ca     32

<210> SEQ ID NO 13
<211> LENGTH: 22
<212> TYPE: DNA
<213> ORGANISM: Artificial sequence
<220> FEATURE:
<223> OTHER INFORMATION: primer

<400> SEQUENCE: 13
ctatagggca cgcgtggtcg ac     22

<210> SEQ ID NO 14
<211> LENGTH: 669
<212> TYPE: DNA
<213> ORGANISM: Glycine max

<400> SEQUENCE: 14
cacaaacaca tacattgtag tatcactttt gtctcggaat ttgttctttt gagttatggc     60
aagcttaaag gttgcatgtg tggttttgat gtgcatggct gtgatgagtg caccaatgat    120
ggtgcaagcc gtgtcatgca atgatgtttc tgtgaaccta gcaccgtgcc tatcttacct    180
gatgcagggt ggagatgttc cagaatcgtg ctgtagcgga gtgaggaaca ttctgggttc    240
tgccagcacc acctttgaca aacaaaccgt gtgcaaatgt cttcagcaag ctgctaataa    300
ctatggcatc aacgacgaat acgctcaggc actccccgcc cgctgcaatg tcagcgtccc    360
ttacaagatc agccgatcca ccaactgcga ctccatcaag ttctaaagga gcgggtagct    420
ttgccaattt cttccgcggg ataatgaggc aacgtatgct gtaacacttg ttatcgttat    480
cattaaaata aagaaagcg agtgtgactc gggttccact catgtgagcc tgttattgta    540
ttagtttctg tttcagatac tctctagtct ttgttgtttc ggtgtgatta aatgtatctt    600
agttgattgt tgctcgcaac aattaatcac gtatttgata taataattcc aagctacttt    660
gattgttgc                                                            669

<210> SEQ ID NO 15
<211> LENGTH: 116
<212> TYPE: PRT
<213> ORGANISM: Glycine max -continued

<400> SEQUENCE: 15

Met Ala Ser Leu Lys Val Ala Cys Val Leu Met Cys Met Ala Val
1               5                   10                  15

Met Ser Ala Pro Met Met Val Gln Ala Val Ser Cys Asn Asp Val Ser
            20                  25                  30

Val Asn Leu Ala Pro Cys Leu Ser Tyr Leu Met Gln Gly Gly Asp Val
        35                  40                  45

Pro Glu Ser Cys Cys Ser Gly Val Arg Asn Ile Leu Gly Ser Ala Ser
    50                  55                  60

Thr Thr Phe Asp Lys Gln Thr Val Cys Lys Cys Leu Gln Gln Ala Ala
65                  70                  75                  80

Asn Asn Tyr Gly Ile Asn Asp Glu Tyr Ala Gln Ala Leu Pro Ala Arg
                85                  90                  95

Cys Asn Val Ser Val Pro Tyr Lys Ile Ser Arg Ser Thr Asn Cys Asp
            100                 105                 110

Ser Ile Lys Phe
        115

<210> SEQ ID NO 16
<211> LENGTH: 22
<212> TYPE: DNA
<213> ORGANISM: Artificial sequence
<220> FEATURE:
<223> OTHER INFORMATION: primer

<400> SEQUENCE: 16
ggaagaagag aatcgggtgg tt                                         22

<210> SEQ ID NO 17
<211> LENGTH: 23
<212> TYPE: DNA
<213> ORGANISM: Artificial sequence
<220> FEATURE:
<223> OTHER INFORMATION: probe

<400> SEQUENCE: 17
attgtgttgt gtggcatggt tat                                        23

<210> SEQ ID NO 18
<211> LENGTH: 23
<212> TYPE: DNA
<213> ORGANISM: Artificial sequence
<220> FEATURE:
<223> OTHER INFORMATION: primer

<400> SEQUENCE: 18
ggcttgttgt gcagtttttg aag                                        23

<210> SEQ ID NO 19
<211> LENGTH: 20
<212> TYPE: DNA
<213> ORGANISM: Artificial sequence
<220> FEATURE:
<223> OTHER INFORMATION: primer

<400> SEQUENCE: 19
aacggccaca agttcgtgat                                            20

<210> SEQ ID NO 20
<211> LENGTH: 20
<212> TYPE: DNA
<213> ORGANISM: Artificial sequence
<220> FEATURE:

```
<223> OTHER INFORMATION: primer

<400> SEQUENCE: 20
accggcgagg gcatcggcta                                              20

<210> SEQ ID NO 21
<211> LENGTH: 20
<212> TYPE: DNA
<213> ORGANISM: Artificial sequence
<220> FEATURE:
<223> OTHER INFORMATION: primer

<400> SEQUENCE: 21
cttcaagggc aagcagacca                                              20

<210> SEQ ID NO 22
<211> LENGTH: 24
<212> TYPE: DNA
<213> ORGANISM: Artificial sequence
<220> FEATURE:
<223> OTHER INFORMATION: primer

<400> SEQUENCE: 22
caaacttgac aaagccacaa ctct                                         24

<210> SEQ ID NO 23
<211> LENGTH: 20
<212> TYPE: DNA
<213> ORGANISM: Artificial sequence
<220> FEATURE:
<223> OTHER INFORMATION: primer

<400> SEQUENCE: 23
ctctcatctc atataaatac                                              20

<210> SEQ ID NO 24
<211> LENGTH: 21
<212> TYPE: DNA
<213> ORGANISM: Artificial sequence
<220> FEATURE:
<223> OTHER INFORMATION: primer

<400> SEQUENCE: 24
ggagaaattg gtgtcgtgga a                                            21

<210> SEQ ID NO 25
<211> LENGTH: 3792
<212> TYPE: DNA
<213> ORGANISM: Artificial sequence
<220> FEATURE:
<223> OTHER INFORMATION: plasmid

<400> SEQUENCE: 25
ccgggctggt actcaatgtg acaaaagaga gataatgaca aatataatgt ataagtgaga    60
tgtttaaaag atcactactc tcgaaataaa attcagtcta attcaatcta gcccaaatgg   120
actagataaa gcaactcaat ttgacaactc tagccgtgct aaccaagaat tggcaattac   180
aaaatatcca aaattgaaac cattttgata tacaaattaa agaaatccgt gcaataaagt   240
ggcctacact acaacaagaa agcagaagaa gaggtaacga agtcgcaagt ggttgcatgt   300
aatgtaagta acaccggcct atagctcacc caccaatata taaaccccc atcaatttc    360 ataaattcat ctaacgtcgc cactcatttc caatctatcc actcatctat ataaaccaca   420
cactacatca cttgttctca ccacattcca aaacacaaac acatacattg tagtatcact   480
```

```
tttgtctcgg aatttgttct tttgagttcc atggcccaca gcaagcacgg cctgaaggag    540
gagatgacca tgaagtacca catggagggc tgcgtgaacg ccacaagtt cgtgatcacc    600 ggcgagggca tcggctaccc cttcaagggc aagcagacca tcaacctgtg cgtgatcgag    660
ggcggccccc tgcccttcag cgaggacatc ctgagcgccg gcttcaagta cggcgaccgg    720
atcttcaccg agtaccccca ggacatcgtg actacttca agaacagctg ccccgccggc    780
tacacctggg gccggagctt cctgttcgag acggcgccg tgtgcatctg taacgtggac    840
atcaccgtga gcgtgaagga gaactgcatc taccacaaga gcatcttcaa cggcgtgaac    900
ttccccgccg acgccccgt gatgaagaag atgaccacca ctgggaggc cagctgcgag    960 aagatcatgc ccgtgcctaa gcagggcatc ctgaagggcg acgtgagcat gtacctgctg   1020
ctgaaggacg gcgccggta ccggtgccag ttcgacaccg tgtacaaggc caagagcgtg   1080
cccagcaaga tgcccgagtg gcacttcatc cagcacaagc tgctgcggga ggaccggagc   1140
gacgccaaga ccagaagtg gcagctgacc gagcacgcca tcgccttccc cagcgccctg   1200
gcctgagagc tcgaatttcc ccgatcgttc aaacatttgg caataaagtt tcttaagatt   1260
gaatcctgtt gccggtcttg cgatgattat catataattt ctgttgaatt acgttaagca   1320
tgtaataatt aacatgtaat gcatgacgtt atttatgaga tgggttttta tgattagagt   1380
cccgcaatta tacatttaat acgcgataga aaacaaaata tagcgcgcaa actaggataa   1440
attatcgcgc gcggtgtcat ctatgttact agatcgggaa ttctagtggc cggcccagct   1500
gatatccatc acactggcgg ccgcactcga ctgaattggt tccggcgcca gcctgctttt   1560
ttgtacaaag ttggcattat aaaaaagcat tgcttatcaa tttgttgcaa cgaacaggtc   1620
actatcagtc aaaataaaat cattatttgg ggcccgagct taagtaacta actaacagga   1680
agagtttgta gaaacgcaaa aaggccatcc gtcaggatgg ccttctgctt agtttgatgc   1740
ctggcagttt atggcgggcg tcctgcccgc caccctccgg gccgttgctt cacaacgttc   1800
aaatccgctc ccggcggatt tgtcctactc aggagagcgt tcaccgacaa caacagata   1860 aaacgaaagg cccagtcttc cgactgagcc tttcgtttta tttgatgcct ggcagttccc   1920
tactctcgct tagtagttag acgtcccga gatccatgct agcggtaata cggttatcca   1980
cagaatcagg ggataacgca ggaaagaaca tgtgagcaaa aggccagcaa aaggccagga   2040
accgtaaaaa ggccgcgttg ctggcgtttt tccataggct ccgcccccct gacgagcatc   2100
acaaaaatcg acgctcaagt cagaggtggc gaaacccgac aggactataa agataccagg   2160
cgtttccccc tggaagctcc ctcgtgcgct ctcctgttcc gaccctgccg cttaccggat   2220
acctgtccgc ctttctccct tcgggaagcg tggcgctttc tcatagctca cgctgtaggt   2280
atctcagttc ggtgtaggtc gttcgctcca agctgggctg tgtgcacgaa ccccccgttc   2340
agcccgaccg ctgcgcctta tccggtaact atcgtcttga gtccaacccg gtaagacacg   2400
acttatcgcc actggcagca gccactggta acaggattag cagagcgagg tatgtaggcg   2460
gtgctacaga gttcttgaag tggtggccta actacggcta cactagaaga acagtatttg   2520
gtatctgcgc tctgctgaag ccagttacct tcggaaaaag agttggtagc tcttgatccg   2580
gcaaacaaac caccgctggt agcggtggtt ttttgtttg caagcagcag attacgcgca   2640
gaaaaaaagg atctcaagaa gatcctttga tcttttctac ggggtctgac gctcagtgga   2700
acgggcccca atctgaataa tgttacaacc aattaaccaa ttctgattag aaaaactcat   2760
cgagcatcaa atgaaactgc aatttattca tatcaggatt atcaatacca tattttgaa   2820 aaagccgttt ctgtaatgaa ggagaaaact caccgaggca gttccatagg atggcaagat   2880
```

```
cctggtatcg gtctgcgatt ccgactcgtc caacatcaat acaacctatt aatttcccct    2940
cgtcaaaaat aaggttatca agtgagaaat caccatgagt gacgactgaa tccggtgaga    3000
atggcaaaag tttatgcatt tctttccaga cttgttcaac aggccagcca ttacgctcgt    3060
catcaaaatc actcgcatca accaaaccgt tattcattcg tgattgcgcc tgagcgagac    3120
gaaatacgcg atcgctgtta aaaggacaat tacaaacagg aatcgaatgc aaccggcgca    3180
ggaacactgc cagcgcatca acaatatttt caccctgaatc aggatattct tctaatacct    3240
ggaatgctgt ttttccgggg atcgcagtgg tgagtaacca tgcatcatca ggagtacgga    3300
taaaatgctt gatggtcgga agaggcataa attccgtcag ccagtttagt ctgaccatct    3360
catctgtaac atcattggca acgctacctt tgccatgttt cagaaacaac tctggcgcat    3420
cgggcttccc atacaagcga tagattgtcg cacctgattg cccgacatta tcgcgagccc    3480
atttataccc atataaatca gcatccatgt tggaatttaa tcgcggcctc gacgtttccc    3540
gttgaatatg gctcataaca ccccttgtat tactgtttat gtaagcagac agttttattg    3600
ttcatgatga tatatttta tcttgtgcaa tgtaacatca gagattttga gacacgggcc    3660
agagctgcag ctggatggca ataatgatt ttattttgac tgatagtgac ctgttcgttg    3720
caacaaattg ataagcaatg ctttcttata atgccaactt tgtacaagaa agctgggtct    3780
agatatctcg ac                                                        3792

<210> SEQ ID NO 26
<211> LENGTH: 8317
<212> TYPE: DNA
<213> ORGANISM: Artificial sequence
<220> FEATURE:
<223> OTHER INFORMATION: plasmid

<400> SEQUENCE: 26
tttgtacaaa cttgttgatg gggttaacat atcataactt cgtataatgt atgctatacg      60
aagttatagg cctggatctt cgaggtcgag cggccgcaga tttaggtgac actatagaat     120
atgcatcact agtaagcttt gctctagatc aaactcacat ccaaacataa catggatatc     180
ttccttacca atcatactaa ttatttgggg ttaaatatta atcattattt ttaagatatt     240
aattaagaaa ttaaaagatt ttttaaaaaa atgtataaaa ttatattatt catgattttt     300
catacatttg attttgataa taaatatatt ttttttaatt tcttaaaaaa tgttgcaaga     360
cacttattag acatagtctt gttctgtta caaaagcatt catcatttaa tacattaaaa     420
aatatttaat actaacagta gaatcttctt gtgagtggtg tgggagtagg caacctggca     480
ttgaaacgag agaaagagag tcagaaccag aagacaaata aaaagtatgc aacaaacaaa     540
tcaaaatcaa agggcaaagg ctggggttgg ctcaattggt tgctacattc aattttcaac     600
tcagtcaacg gttgagattc actctgactt ccccaatcta agccgcggat gcaaacggtt     660
gaatctaacc cacaatccaa tctcgttact tagggctttt ccgtcatta actcacccct     720 gccacccggt ttccctataa attggaactc aatgctcccc tctaaactcg tatcgcttca     780
gagttgagac caagacacac tcgttcatat atctctctgc tcttctcttc tcttctacct     840
ctcaaggtac ttttcttctc cctctaccaa atcctagatt ccgtggttca atttcggatc     900
ttgcacttct ggtttgcttt gccttgcttt tcctcaact gggtccatct aggatccatg     960
tgaaactcta ctctttcttt aatatctgcg gaatacgcgt ttgactttca gatcagtcg    1020 aaatcatttc ataattgcct ttctttcttt tagcttatga gaaataaaat cacttttttt    1080
ttatttcaaa ataaaccttg ggccttgtgc tgactgagat ggggtttggt gattacagaa    1140
```

```
ttttagcgaa ttttgtaatt gtacttgttt gtctgtagtt ttgttttgtt ttcttgtttc   1200
tcatacattc cttaggcttc aattttattc gagtataggt cacaatagga attcaaactt   1260
tgagcagggg aattaatccc ttccttcaaa tccagtttgt ttgtatatat gtttaaaaaa   1320 tgaaacttttt gctttaaatt ctattataac ttttttttatg gctgaaattt ttgcatgtgt   1380
ctttgctctc tgttgtaaat ttactgttta ggtactaact ctaggcttgt tgtgcagttt   1440
ttgaagtata accatgccac acaacacaat ggcggccacc gcttccagaa ccacccgatt   1500
ctcttcttcc tcttcacacc ccaccttccc caaacgcatt actagatcca ccctccctct   1560
ctctcatcaa accctcacca aacccaacca cgctctcaaa atcaaatgtt ccatctccaa   1620
accccccacg gcggcgccct tcaccaagga agcgccgacc acggagccct tcgtgtcacg   1680
gttcgcctcc ggcgaacctc gcaagggcgc ggacatcctt gtggaggcgc tggagaggca   1740
gggcgtgacg acggtgttcg cgtaccccgg cggtgcgtcg atggagatcc accaggcgct   1800
cacgcgctcc gccgccatcc gcaacgtgct cccgcgccac gagcagggcg gcgtcttcgc   1860
cgccgaaggc tacgcgcgtt cctccggcct ccccggcgtc tgcattgcca cctccggccc   1920
cggcgccacc aacctcgtga gcggcctcgc cgacgcttta atggacagcg tcccagtcgt   1980
cgccatcacc ggccaggtcg cccgccggat gatcggcacc gacgccttcc aagaaacccc   2040
gatcgtggag gtgagcagat ccatcacgaa gcacaactac ctcatcctcg acgtcgacga   2100 catccccgc gtcgtcgccg aggctttctt cgtcgccacc tccggccgcc ccggtccggt   2160
cctcatcgac attcccaaag acgttcagca gcaactcgcc gtgcctaatt gggacgagcc   2220
cgttaacctc cccggttacc tcgccaggct gcccaggccc ccgccgagg cccaattgga   2280 acacattgtc agactcatca tggaggccca aaagcccgtt ctctacgtcg gcggtggcag   2340
tttgaattcc agtgctgaat tgaggcgctt tgttgaactc actggtattc ccgttgctag   2400
cactttaatg ggtcttggaa cttttcctat tggtgatgaa tattcccttc agatgctggg   2460
tatgcatggt actgtttatg ctaactatgc tgttgacaat agtgatttgt tgcttgcctt   2520
tggggtaagg tttgatgacc gtgttactgg gaagcttgag gcttttgcta gtagggctaa   2580
gattgttcac attgatattg attctgccga gattgggaag aacaagcagg cgcacgtgtc   2640
ggtttgcgcg gatttgaagt tggccttgaa gggaattaat atgattttgg aggagaaagg   2700
agtggagggt aagtttgatc ttggaggttg gagagaagag attaatgtgc agaaacacaa   2760
gtttccattg ggttacaaga cattccagga cgcgatttct ccgcagcatg ctatcgaggt   2820
tcttgatgag ttgactaatg gagatgctat tgttagtact ggggttgggc agcatcaaat   2880
gtgggctgcg cagttttaca agtacaagag accgaggcag tggttgacct caggggggtct   2940 tggagccatg ggttttggat tgcctgcggc tattggtgct gctgttgcta accctggggc   3000
tgttgtggtt gacattgatg gggatggtag tttcatcatg aatgttcagg agttggccac   3060
tataagagtg gagaatctcc cagttaagat attgttgttg aacaatcagc atttgggtat   3120
ggtggttcag ttgaggata ggttctacaa gtccaataga gctcacacct atcttggaga   3180
tccgtctagc gagagcgaga tattcccaaa catgctcaag tttgctgatg cttgtgggat   3240
accggcagcg cgagtgacga agaaggaaga gcttagagcg gcaattcaga gaatgttgga   3300
cacccctggc ccctaccttc ttgatgtcat tgtgccccat caggagcatg tgttgccgat   3360 gattccagt aatggatcct tcaaggatgt gataactgag ggtgatggta gaacgaggta   3420
ctgattgcct agaccaaatg ttccttgatg cttgttttgt acaatatata taagataatg   3480
ctgtcctagt tgcaggattt ggcctgtggt gagcatcata gtctgtagta gttttggtag   3540
```

```
caagacattt tatttttcctt ttatttaact tactacatgc agtagcatct atctatctct    3600
gtagtctgat atctcctgtt gtctgtattg tgccgttgga ttttttgctg tagtgagact    3660
gaaaatgatg tgctagtaat aatatttctg ttagaaatct aagtagagaa tctgttgaag    3720
aagtcaaaag ctaatggaat caggttacat attcaatgtt tttctttttt tagcggttgg    3780
tagacgtgta gattcaactt ctcttggagc tcacctaggc aatcagtaaa atgcatattc    3840
ctttttaac ttgccattta tttacttta gtggaaattg tgaccaattt gttcatgtag    3900
aacggatttg gaccattgcg tccacaaaac gtctcttttg ctcgatcttc acaaagcgat    3960
accgaaatcc agagatagtt ttcaaaagtc agaaatggca aagttataaa tagtaaaaca    4020
gaatagatgc tgtaatcgac ttcaataaca agtggcatca cgtttctagt tctagaccca    4080
tcagatcgaa ttaacatatc ataacttcgt ataatgtatg ctatacgaag ttataggcct    4140
ggatccacta gttctagagc ggccgctcga gggggggccc ggtaccggcg cgccgttcta    4200
tagtgtcacc taaatcgtat gtgtatgata cataaggtta tgtattaatt gtagccgcgt    4260
tctaacgaca atatgtccat atggtgcact ctcagtacaa tctgctctga tgccgcatag    4320
ttaagccagc cccgacaccc gccaacaccc gctgacgcgc cctgacgggc ttgtctgctc    4380
ccggcatccg cttacagaca agctgtgacc gtctccggga gctgcatgtg tcagaggttt    4440
tcaccgtcat caccgaaacg cgcgagacga aagggcctcg tgatacgcct atttttatag    4500
gttaatgtca tgaccaaaat cccttaacgt gagttttcgt tccactgagc gtcagacccc    4560
gtagaaaaga tcaaaggatc ttcttgagat cctttttttc tgcgcgtaat ctgctgcttg    4620
caaacaaaaa aaccaccgct accagcggtg gtttgtttgc cggatcaaga gctaccaact    4680
ctttttccga aggtaactgg cttcagcaga gcgcagatac caaatactgt ccttctagtg    4740
tagccgtagt taggccacca cttcaagaac tctgtagcac cgcctacata cctcgctctg    4800
ctaatcctgt taccagtggc tgctgccagt ggcgataagt cgtgtcttac cgggttggac    4860
tcaagacgat agttaccgga taaggcgcag cggtcgggct gaacgggggg ttcgtgcaca    4920
cagcccagct tggagcgaac gacctacacc gaactgagat acctacagcg tgagcattga    4980
gaaagcgcca cgcttcccga agggagaaag gcggacaggt atccggtaag cggcagggtc    5040
ggaacaggag agcgcacgag ggagcttcca gggggaaacg cctggtatct ttatagtcct    5100
gtcgggtttc gccacctctg acttgagcgt cgatttttgt gatgctcgtc agggggggcgg    5160
agcctatgga aaaacgccag caacgcggcc ttttttacggt tcctggcctt ttgctggcct    5220
tttgctcaca tgttctttcc tgcgttatcc cctgattctg tggataaccg tattaccgcc    5280
tttgagtgag ctgataccgc tcgccgcagc cgaacgaccg agcgcagcga gtcagtgagc    5340
gaggaagcgg aagagcgccc aatacgcaaa ccgcctctcc ccgcgcgttg gccgattcat    5400
taatgcaggt tgatcagatc tcgatcccgc gaaattaata cgactcacta tagggagacc    5460
acaacggttt ccctctagaa ataattttgt ttaactttaa gaaggagata tacccatgga    5520
aaagcctgaa ctcaccgcga cgtctgtcga agtttctg atcgaaaagt cgacagcgt    5580
ctccgacctg atgcagctct cggagggcga agaatctcgt gctttcagct tcgatgtagg    5640
agggcgtgga tatgtcctgc gggtaaatag ctgcgccgat ggtttctaca agatcgtta    5700
tgtttatcgg cactttgcat cggccgcgct cccgattccg gaagtgcttg acattgggga    5760
attcagcgag agcctgacct attgcatctc ccgccgtgca cagggtgtca cgttgcaaga    5820
cctgcctgaa accgaactgc ccgctgttct gcagccggtc gcggaggcta tggatgcgat    5880
cgctgcggcc gatcttagcc agacgagcgg gttcggccca ttcggaccgc aaggaatcgg    5940
```

```
tcaatacact acatggcgtg atttcatatg cgcgattgct gatccccatg tgtatcactg    6000
gcaaactgtg atggacgaca ccgtcagtgc gtccgtcgcg caggctctcg atgagctgat    6060
gctttgggcc gaggactgcc ccgaagtccg gcacctcgtg cacgcggatt tcggctccaa    6120
caatgtcctg acgacaatg gccgcataac agcggtcatt gactggagcg aggcgatgtt     6180
cggggattcc caatacgagg tcgccaacat cttcttctgg aggccgtggt tggcttgtat    6240
ggagcagcag acgcgctact tcgagcggag gcatccggag cttgcaggat cgccgcggct    6300
ccgggcgtat atgctccgca ttggtcttga ccaactctat cagagcttgg ttgacggcaa    6360
tttcgatgat gcagcttggg cgcagggtcg atgcgacgca atcgtccgat ccggagccgg    6420
gactgtcggg cgtacacaaa tcgcccgcag aagcgcggcc gtctggaccg atggctgtgt    6480
agaagtactc gccgatagtg gaaaccgacg ccccagcact cgtccgaggg caaaggaata    6540
gtgaggtaca gcttggatcg atccggctgc taacaaagcc cgaaaggaag ctgagttggc    6600
tgctgccacc gctgagcaat aactagcata accccttggg gcctctaaac gggtcttgag    6660
gggttttttg ctgaaaggag gaactatatc cggatgatcg ggcgcgccgg tacccatcaa    6720
ccactttgta caagaaagct gggtctagat atctcgaccc gggctggtac tcaatgtgac    6780
aaaagagaga taatgacaaa tataatgtat aagtgagatg tttaaaagat cactactctc    6840
gaaataaaat tcagtctaat tcaatctagc ccaaatggac tagataaagc aactcaattt    6900
gacaactcta gccgtgctaa ccaagaattg gcaattacaa aatatccaaa attgaaacca    6960
ttttgatata caaattaaag aaatccgtgc aataaagtgg cctacactac aacaagaaag    7020
cagaagaaga ggtaacgaag tcgcaagtgg ttgcatgtaa tgtaagtaac accggcctat    7080
agctcaccca ccaatataat aaaccccccat caattttcat aaattcatct aacgtcgcca    7140
ctcatttcca atctatccac tcatctatat aaacaccaca ctacatcact tgttctcacc    7200
acattccaaa acacaaacac atacattgta gtatcacttt tgtctcggaa tttgttcttt    7260
tgagttccat ggcccacagc aagcacggcc tgaaggagga gatgaccatg aagtaccaca    7320
tggagggctg cgtgaacggc cacaagttcg tgatcaccgg cgagggcatc ggctacccct    7380
tcaagggcaa gcagaccatc aacctgtgcg tgatcgaggg cggccccctg cccttcagcg    7440
aggacatcct gagcgccggc ttcaagtacg gcgaccggat cttcaccgag tacccccagg    7500
acatcgtgga ctacttcaag aacagctgcc ccgccggcta cacctggggc cggagcttcc    7560
tgttcgagga cggcgccgtg tgcatctgta acgtggacat caccgtgagc gtgaaggaga    7620
actgcatcta ccacaagagc atcttcaacg gcgtgaactt ccccgccgac ggccccgtga    7680
tgaagaagat gaccaccaac tgggaggcca gctgcgagaa gatcatgccc gtgcctaagc    7740
agggcatcct gaagggcgac gtgagcatgt acctgctgct gaaggacggc ggccggtacc    7800
ggtgccagtt cgacaccgtg tacaaggcca agagcgtgcc cagcaagatg cccgagtggc    7860
acttcatcca gcacaagctg ctgcgggagg accgagcga cgccaagaac cagaagtggc    7920
agctgaccga gcacgccatc gccttcccca gcgccctggc ctgagagctc gaatttcccc    7980
gatcgttcaa acatttggca ataaagtttc ttaagattga atcctgttgc cggtcttgcg    8040
atgattatca tataatttct gttgaattac gttaagcatg taataattaa catgtaatgc    8100
atgacgttat ttatgagatg ggttttttatg attagagtcc cgcaattata catttaatac    8160
gcgatagaaa acaaaatata gcgcgcaaac taggataaat tatcgcgcgc ggtgtcatct    8220
atgttactag atcgggaatt ctagtggccg gccagctga tatccatcac actggcggcc    8280
gcactcgact gaattggttc cggcgccagc ctgcttt                            8317
```

<210> SEQ ID NO 27
<211> LENGTH: 8409
<212> TYPE: DNA
<213> ORGANISM: Artificial sequence
<220> FEATURE:
<223> OTHER INFORMATION: plasmid

<400> SEQUENCE: 27

| | | | | | |
|---|---|---|---|---|---|
| atcaaccact | ttgtacaaga | aagctgaacg | agaaacgtaa | aatgatataa | atatcaatat | 60 |
| attaaattag | attttgcata | aaaaacagac | tacataatac | tgtaaaacac | aacatatcca | 120 |
| gtcactatgg | tcgacctgca | gactggctgt | gtataaggga | gcctgacatt | tatattcccc | 180 |
| agaacatcag | gttaatggcg | tttttgatgt | cattttcgcg | gtggctgaga | tcagccactt | 240 |
| cttccccgat | aacggagacc | ggcacactgg | ccatatcggt | ggtcatcatg | cgccagcttt | 300 |
| catccccgat | atgcaccacc | gggtaaagtt | cacgggagac | tttatctgac | agcagacgtg | 360 |
| cactggccag | ggggatcacc | atccgtcgcc | cgggcgtgtc | aataatatca | ctctgtacat | 420 |
| ccacaaacag | acgataacgg | ctctctcttt | tataggtgta | aaccttaaac | tgcatttcac | 480 |
| cagcccctgt | tctcgtcagc | aaaagagccg | ttcatttcaa | taaaccgggc | gacctcagcc | 540 |
| atcccttcct | gattttccgc | tttccagcgt | tcggcacgca | gacgacgggc | ttcattctgc | 600 |
| atggttgtgc | ttaccagacc | ggagatattg | acatcatata | tgccttgagc | aactgatagc | 660 |
| tgtcgctgtc | aactgtcact | gtaatacgct | gcttcatagc | atacctcttt | ttgacatact | 720 |
| tcgggtatac | atatcagtat | atattcttat | accgcaaaaa | tcagcgcgca | aatacgcata | 780 |
| ctgttatctg | gcttttagta | agccggatcc | agatctttac | gccccgccct | gccactcatc | 840 |
| gcagtactgt | tgtaattcat | taagcattct | gccgacatgg | aagccatcac | aaacggcatg | 900 |
| atgaacctga | atcgccagcg | gcatcagcac | cttgtcgcct | tgcgtataat | atttgcccat | 960 |
| ggtgaaaacg | ggggcgaaga | agttgtccat | attggccacg | tttaaatcaa | aactggtgaa | 1020 |
| actcacccag | ggattggctg | agacgaaaaa | catattctca | ataaaccctt | tagggaaata | 1080 |
| ggccaggttt | tcaccgtaac | acgccacatc | ttgcgaatat | atgtgtagaa | actgccggaa | 1140 |
| atcgtcgtgg | tattcactcc | agagcgatga | aaacgtttca | gtttgctcat | ggaaaacggt | 1200 |
| gtaacaaggg | tgaacactat | cccatatcac | cagctcaccg | tctttcattg | ccatacggaa | 1260 |
| ttccggatga | gcattcatca | ggcgggcaag | aatgtgaata | aaggccggat | aaaacttgtg | 1320 |
| cttatttttc | tttacggtct | ttaaaaaggc | cgtaatatcc | agctgaacgg | tctggttata | 1380 |
| ggtacattga | gcaactgact | gaaatgcctc | aaaatgttct | ttacgatgcc | attgggatat | 1440 |
| atcaacggtg | gtatatccag | tgatttttt | ctccatttta | gcttccttag | ctcctgaaaa | 1500 |
| tctcgacgga | tcctaactca | aaatccacac | attatacgag | ccggaagcat | aaagtgtaaa | 1560 |
| gcctggggtg | cctaatgcgg | ccgccaatat | gactggatat | gttgtgtttt | acagtattat | 1620 |
| gtagtctgtt | ttttatgcaa | aatctaattt | aatatattga | tatttatatc | attttacgtt | 1680 |
| tctcgttcag | cttttttgta | caaacttgtt | gatggggtta | acatatcata | acttcgtata | 1740 |
| atgtatgcta | tacgaagtta | taggcctgga | tcttcgaggt | cgagcggccg | cagatttagg | 1800 |
| tgacactata | gaatatgcat | cactagtaag | ctttgctcta | gatcaaactc | acatccaaac | 1860 |
| ataacatgga | tatcttcctt | accaatcata | ctaattattt | tgggttaaat | attaatcatt | 1920 |
| atttttaaga | tattaattaa | gaaattaaaa | gatttttaa | aaaaatgtat | aaaattatat | 1980 |
| tattcatgat | ttttcataca | tttgattttg | ataataaata | tatttttttt | aatttcttaa | 2040 |
| aaaatgttgc | aagacactta | ttagacatag | tcttgttctg | tttacaaaag | cattcatcat | 2100 |

```
ttaatacatt aaaaaatatt taatactaac agtagaatct tcttgtgagt ggtgtgggag    2160
taggcaacct ggcattgaaa cgagagaaag agagtcagaa ccagaagaca aataaaaagt    2220
atgcaacaaa caaatcaaaa tcaaagggca aaggctgggg ttggctcaat tggttgctac    2280
attcaatttt caactcagtc aacggttgag attcactctg acttccccaa tctaagccgc    2340
ggatgcaaac ggttgaatct aacccacaat ccaatctcgt tacttagggg cttttccgtc    2400
attaactcac ccctgccacc cggtttccct ataaattgga actcaatgct cccctctaaa    2460
ctcgtatcgc ttcagagttg agaccaagac acactcgttc atatatctct ctgctcttct    2520
cttctcttct acctctcaag gtactttttct tctccctcta ccaaatccta gattccgtgg   2580
ttcaatttcg gatcttgcac ttctggtttg ctttgccttg ctttttcctc aactgggtcc    2640
atctaggatc catgtgaaac tctactcttt ctttaatatc tgcggaatac gcgtttgact    2700
ttcagatcta gtcgaaatca tttcataatt gcctttcttt cttttagctt atgagaaata    2760
aaatcacttt tttttttattt caaaataaac cttgggcctt gtgctgactg agatgggtt    2820 tggtgattac agaattttag cgaattttgt aattgtactt gtttgtctgt agttttgttt    2880
tgttttcttg tttctcatac attccttagg cttcaatttt attcgagtat aggtcacaat    2940
aggaattcaa actttgagca ggggaattaa tcccttcctt caaatccagt tgtttgtat    3000 atatgtttaa aaaatgaaac ttttgcttta aattctatta taactttttt tatggctgaa    3060 attttgcat gtgtctttgc tctctgttgt aaatttactg tttaggtact aactctaggc     3120
ttgttgtgca gtttttgaag tataaccatg ccacacaaca caatggcggc caccgcttcc    3180
agaaccaccc gattctcttc ttcctcttca caccccacct tccccaaacg cattactaga    3240
tccaccctcc ctctctctca tcaaaccctc accaaacccca accacgctct caaaatcaaa   3300
tgttccatct ccaaaccccc cacggcggcg cccttcacca aggaagcgcc gaccacggag    3360
cccttcgtgt cacggttcgc ctccggcgaa cctcgcaagg gcgcggacat ccttgtggag    3420
gcgctggaga ggcagggcgt gacgacggtg ttcgcgtacc ccggcggtgc gtcgatggag    3480
atccaccagg cgctcacgcg ctccgccgcc atccgcaacg tgctcccgcg ccacgagcag    3540
ggcggcgtct tcgccgccga aggctacgcg cgttcctccg gcctccccgg cgtctgcatt    3600
gccacctccg gccccggcgc caccaacctc gtgagcggcc tcgccgacgc tttaatggac    3660
agcgtcccag tcgtcgccat caccggccag gtcgcccgcc ggatgatcgg caccgacgcc    3720
ttccaagaaa ccccgatcgt ggaggtgagc agatccatca cgaagcacaa ctacctcatc    3780
ctcgacgtcg acgacatccc ccgcgtcgtc gccgaggctt tcttcgtcgc cacctccggc    3840
cgccccggtc cggtcctcat cgacattccc aaagacgttc agcagcaact cgccgtgcct    3900
aattgggacg agcccgttaa cctccccggt tacctcgcca ggctgcccag gccccccgcc    3960
gaggcccaat tggaacacat tgtcagactc atcatggagg cccaaaagcc cgttctctac    4020
gtcggcggtg gcagtttgaa ttccagtgct gaattgaggc gctttgttga actcactggt    4080
attcccgttg ctagcacttt aatgggtctt ggaactttc ctattggtga tgaatattcc     4140
cttcagatgc tgggtatgca tggtactgtt tatgctaact atgctgttga caatagtgat    4200
ttgttgcttg ccttttgggt aaggtttgat gaccgtgtta ctgggaagct tgaggctttt    4260
gctagtaggg ctaagattgt tcacattgat attgattctg ccgagattgg gaagaacaag    4320
caggcgcacg tgtcggtttg cgcggatttg aagttggcct tgaagggaat taatatgatt    4380
ttggaggaga aaggagtgga gggtaagttt gatcttggag gttggagaga agagattaat    4440
gtgcagaaac acaagtttcc attgggttac aagacattcc aggacgcgat ttctccgcag    4500
```

```
catgctatcg aggttcttga tgagttgact aatggagatg ctattgttag tactggggtt    4560
gggcagcatc aaatgtgggc tgcgcagttt tacaagtaca agagaccgag gcagtggttg    4620
acctcagggg gtcttggagc catgggtttt ggattgcctg cggctattgg tgctgctgtt    4680
gctaaccctg gggctgttgt ggttgacatt gatggggatg gtagtttcat catgaatgtt    4740
caggagttgg ccactataag agtggagaat ctcccagtta agatattgtt gttgaacaat    4800
cagcatttgg gtatggtggt tcagttggag gataggttct acaagtccaa tagagctcac    4860
acctatcttg gagatccgtc tagcgagagc gagatattcc caaacatgct caagtttgct    4920
gatgcttgtg ggataccggc agcgcgagtg acgaagaagg aagagcttag agcggcaatt    4980
cagagaatgt tggacacccc tggcccctac cttcttgatg tcattgtgcc ccatcaggag    5040
catgtgttgc cgatgattcc cagtaatgga tccttcaagg atgtgataac tgagggtgat    5100
ggtagaacga ggtactgatt gcctagacca aatgttcctt gatgcttgtt ttgtacaata    5160
tatataagat aatgctgtcc tagttgcagg atttggcctg tggtgagcat catagtctgt    5220
agtagttttg gtagcaagac attttatttt cctttattt aacttactac atgcagtagc    5280
atctatctat ctctgtagtc tgatatctcc tgttgtctgt attgtgccgt ggatttttt    5340
gctgtagtga gactgaaaat gatgtgctag taataatatt tctgttagaa atctaagtag    5400
agaatctgtt gaagaagtca aaagctaatg gaatcaggtt acatattcaa tgttttctt    5460
tttttagcgg ttggtagacg tgtagattca acttctcttg gagctcacct aggcaatcag    5520
taaaatgcat attccttttt taacttgcca tttatttact tttagtggaa attgtgacca    5580
atttgttcat gtagaacgga tttggaccat tgcgtccaca aaacgtctct tttgctcgat    5640
cttcacaaag cgataccgaa atccagagat agttttcaaa agtcagaaat ggcaaagtta    5700
taaatagtaa aacagaatag atgctgtaat cgacttcaat aacaagtggc atcacgtttc    5760
tagttctaga cccatcagat cgaattaaca tatcataact tcgtataatg tatgctatac    5820
gaagttatag gcctggatcc actagttcta gagcggccgc tcgaggggg gcccggtacc    5880
ggcgcgccgt tctatagtgt cacctaaatc gtatgtgtat gatacataag gttatgtatt    5940
aattgtagcc gcgttctaac gacaatatgt ccatatggtg cactctcagt acaatctgct    6000
ctgatgccgc atagttaagc cagccccgac acccgccaac acccgctgac gcgccctgac    6060
gggcttgtct gctcccggca tccgcttaca gacaagctgt gaccgtctcc gggagctgca    6120
tgtgtcagag gttttcaccg tcatcaccga aacgcgcgag acgaaagggc ctcgtgatac    6180
gcctattttt ataggttaat gtcatgacca aaatccctta acgtgagttt tcgttccact    6240
gagcgtcaga ccccgtagaa aagatcaaag gatcttcttg agatcctttt tttctgcgcg    6300
taatctgctg cttgcaaaca aaaaaaccac cgctaccagc ggtggtttgt ttgccggatc    6360
aagagctacc aactcttttt ccgaaggtaa ctggcttcag cagagcgcag ataccaaata    6420
ctgtcctct agtgtagccg tagttaggcc accacttcaa gaactctgta gcaccgccta    6480
catacctcgc tctgctaatc ctgttaccag tggctgctgc cagtggcgat aagtcgtgtc    6540
ttaccgggtt ggactcaaga cgatagttac cggataaggc gcagcggtcg ggctgaacgg    6600
ggggttcgtg cacacagccc agcttggagc gaacgaccta caccgaactg agatacctac    6660
agcgtgagca ttgagaaagc gccacgcttc ccgaagggag aaaggcggac aggtatccgg    6720
taagcggcag ggtcggaaca ggagagcgca cgagggagct tccaggggga aacgcctggt    6780
atctttatag tcctgtcggg tttcgccacc tctgacttga gcgtcgattt ttgtgatgct    6840
cgtcaggggg gcggagccta tggaaaaacg ccagcaacgc ggcctttta cggttcctgg    6900
```

```
cctttttgctg gccttttgct cacatgttct ttcctgcgtt atccctgat tctgtggata    6960
accgtattac cgcctttgag tgagctgata ccgctcgccg cagccgaacg accgagcgca    7020
gcgagtcagt gagcgaggaa gcggaagagc gcccaatacg caaaccgcct ctccccgcgc    7080
gttggccgat tcattaatgc aggttgatca gatctcgatc ccgcgaaatt aatacgactc    7140
actataggga gaccacaacg gtttccctct agaaataatt ttgtttaact ttaagaagga    7200
gatatacccca tggaaaagcc tgaactcacc gcgacgtctg tcgagaagtt tctgatcgaa    7260
aagttcgaca gcgtctccga cctgatgcag ctctcggagg gcgaagaatc tcgtgctttc    7320
agcttcgatg taggagggcg tggatatgtc ctgcgggtaa atagctgcgc cgatggtttc    7380
tacaaagatc gttatgttta tcggcacttt gcatcggccg cgctcccgat tccggaagtg    7440
cttgacattg gggaattcag cgagagcctg acctattgca tctcccgccg tgcacagggt    7500
gtcacgttgc aagacctgcc tgaaaccgaa ctgcccgctg ttctgcagcc ggtcgcggag    7560
gctatggatg cgatcgctgc ggccgatctt agccagacga gcgggttcgg cccattcgga    7620
ccgcaaggaa tcggtcaata cactacatgg cgtgatttca tatgcgcgat tgctgatccc    7680
catgtgtatc actggcaaac tgtgatggac gacaccgtca gtgcgtccgt cgcgcaggct    7740
ctcgatgagc tgatgctttg gccgaggac tgccccgaag tccggcacct cgtgcacgcg    7800
gatttcggct ccaacaatgt cctgacggac aatggccgca taacagcggt cattgactgg    7860
agcgaggcga tgttcgggga ttcccaatac gaggtcgcca acatcttctt ctggaggccg    7920
tggttggctt gtatggagca gcagacgcgc tacttcgagc ggaggcatcc ggagcttgca    7980
ggatcgccgc ggctccgggc gtatatgctc cgcattggtc ttgaccaact ctatcagagc    8040
ttggttgacg gcaatttcga tgatgcagct tgggcgcagg gtcgatgcga cgcaatcgtc    8100
cgatccggag ccgggactgt cgggcgtaca caaatcgccc gcagaagcgc ggccgtctgg    8160
accgatggct gtgtagaagt actcgccgat agtggaaacc gacgccccag cactcgtccg    8220
agggcaaagg aatagtgagg tacagcttgg atcgatccgg ctgctaacaa agcccgaaag    8280
gaagctgagt tggctgctgc caccgctgag caataactag cataacccct tggggcctct    8340
aaacgggtct tgagggtttt tttgctgaaa ggaggaacta tatccggatg atcgggcgcg    8400
ccggtaccc                                                            8409
```

<210> SEQ ID NO 28
<211> LENGTH: 100
<212> TYPE: DNA
<213> ORGANISM: Artificial sequence
<220> FEATURE:
<223> OTHER INFORMATION: recombination site

<400> SEQUENCE: 28

```
caaataatga ttttattttg actgatagtg acctgttcgt tgcaacaaat tgataagcaa     60
tgcttttttta taatgccaac tttgtacaaa aaagcaggct                         100
```

<210> SEQ ID NO 29
<211> LENGTH: 100
<212> TYPE: DNA
<213> ORGANISM: Artficial sequence
<220> FEATURE:
<223> OTHER INFORMATION: recombination site

<400> SEQUENCE: 29

```
taatgatttt attttgcaaa actgatagtg acctgttcgt tgcaacaaat tgataagcaa     60
tgcttttctta taatgccaac tttgtacaag aaagctgggt                         100
```

```
<210> SEQ ID NO 30
<211> LENGTH: 125
<212> TYPE: DNA
<213> ORGANISM: Artificial sequence
<220> FEATURE:
<223> OTHER INFORMATION: recombination site

<400> SEQUENCE: 30
acaagtttgt acaaaaaagc tgaacgagaa acgtaaaatg atataaatat caatatatta      60
aattagattt tgcataaaaa acagactaca taatactgta aaacacaaca tatccagtca     120
ctatg                                                                 125

<210> SEQ ID NO 31
<211> LENGTH: 125
<212> TYPE: DNA
<213> ORGANISM: Artificial sequence
<220> FEATURE:
<223> OTHER INFORMATION: recombination site

<400> SEQUENCE: 31
accactttgt acaagaaagc tgaacgagaa acgtaaaatg atataaatat caatatatta      60
aattagattt tgcataaaaa acagactaca taatactgta aaacacaaca tatccagtca     120
ctatg                                                                 125

<210> SEQ ID NO 32
<211> LENGTH: 21
<212> TYPE: DNA
<213> ORGANISM: Artificial sequence
<220> FEATURE:
<223> OTHER INFORMATION: recombination site

<400> SEQUENCE: 32
caagtttgta caaaaaagca g                                                21

<210> SEQ ID NO 33
<211> LENGTH: 21
<212> TYPE: DNA
<213> ORGANISM: Artificial sequence
<220> FEATURE:
<223> OTHER INFORMATION: recombination site

<400> SEQUENCE: 33
cagctttctt gtacaaagtg g                                                21
```

SOYBEAN PROMOTER LTP4 AND FLOWER-PREFERRED EXPRESSION THEREOF IN TRANSGENIC PLANTS

This application claims priority to U.S. provisional Application No. 61/014,567 filed Dec. 18, 2007, the entire contents of which are hereby incorporated by reference.

FIELD OF THE INVENTION

The present invention relates to the field of plant molecular biology, more particularly to regulation of gene expression in plants.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities can be incorporated properly into the plant's genome. The newly integrated gene (or genes) coding sequence can then be expressed in the plant cell to exhibit the desired new trait or characteristic. It is important that appropriate regulatory signals be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis may occur in other tissues at reduced levels). Since patterns of expression of a chimeric gene (or genes) introduced into a plant are controlled using promoters, there is an ongoing interest in the isolation of novel promoters that are capable of controlling the expression of a chimeric gene (or genes) at certain levels in specific tissue types or at specific plant developmental stages.

Among the most commonly used promoters are the nopaline synthase (NOS) promoter (Ebert et al., Proc. Natl. Acad. Sci. U.S.A. 84:5745-5749 (1987)); the octapine synthase (OCS) promoter, caulimovirus promoters such as the cauliflower mosaic virus (CaMV) 19S promoter (Lawton et al., Plant Mol. Biol. 9:315-324 (1987)); the CaMV 35S promoter (Odell et al., Nature 313:810-812 (1985)), and the figwort mosaic virus 35S promoter (Sanger et al., Plant Mol. Biol. 14:433-43 (1990)); the light inducible promoter from the small subunit of rubisco (Pellegrineschi et al., Biochem. Soc. Trans. 23(2):247-250 (1995)); the Adh promoter (Walker et al., Proc. Natl. Acad. Sci. U.S.A. 84:6624-66280 (1987)); the sucrose synthase promoter (Yang et al., Proc. Natl. Acad. Sci. U.S.A. 87:4144-4148 (1990)); the R gene complex promoter (Chandler et al., Plant Cell 1:1175-1183 (1989)); the chlorophyll a/b binding protein gene promoter; and the like.

An angiosperm flower is a complex structure generally consisting of a pedicel, sepals, petals, stamens, and a pistil. A stamen comprises a filament and an anther in which the male gametophyte pollens reside. A pistil comprises a stigma, style and ovary. An ovary contains one or more ovules in which the female gametophyte embryo sac, egg cell, central cell, and other specialized cells reside. Flower promoters in general include promoters that direct gene expression in any of the above tissues or cell types.

Lipid transfer protein (LTP) genes have been isolated from barley (Federico et al., Plant Mol. Biol. 57:35-51 (2005)), strawberry (Yubero-Serrano et al, J. Exp. Bot. 54:1865-1877 (2003)), *Arabidopsis* (Thoma et al., Plant Physiol. 105:35-45 (1994)), Norway spruce (Sabala et al., Plant Mol. Biol. 42:461-478 (2000)), rice (Vignols et al., Gene 142:265-270 (1994)), carrot (Toonen et al., Plant J. 12:1213-1221 (1997)), *Brassica napus* (Sohal et al., Plant Mol. Biol. 41:75-87 (1999)), *Sorghum vulgare* (Pelese-Siebenbourg et al., Gene 148:305-308 (1994)), and other plant species. The reported LTP genes are known to have various expression patterns in respective plants. However, there remains a lack of soybean LTP genes or flower-preferred expression of LTP genes. LTP assays have been described (Jean-Claude Kader, Annual Review of Plant Phys. and Plant Mol. Biol. 47: 627-654 (1996). Plant LTPs have eight cysteine residues located at conserved positions. The cysteine residues are engaged in four disulfide bridges (Jean-Claude Kader, Annual Review of Plant Phys. and Plant Mol. Biol. 47: 627-654 (1996)).

Although advances in technology provide greater success in transforming plants with chimeric genes, there is still a need for preferred expression of such genes in desired plants. Often times it is desired to selectively express target genes in a specific tissue because of toxicity or efficacy concerns. For example, flower tissue is a type of tissue where preferred expression is desirable and there remains a need for promoters that preferably initiate transcription in flower tissue. Promoters that initiate transcription preferably in flower tissue control genes involved in flower development and flower abortion.

SUMMARY OF THE INVENTION

Compositions and methods for regulating gene expression in a plant are provided. One aspect is for an isolated polynucleotide comprising: a) a nucleotide sequence comprising the sequence set forth in SEQ ID NO:1 or a full-length complement thereof; or b) a nucleotide sequence comprising a sequence having at least 90% sequence identity, based on the BLASTN method of alignment, when compared to the sequence set forth in SEQ ID NO:1; wherein said nucleotide sequence is a promoter.

Other embodiments include recombinant DNA constructs comprising a polynucleotide sequence of the present invention operably linked to a heterologous sequence. Additional, some embodiments provide for transgenic plant cells, transient and stable, transgenic plant seeds, as well as transgenic plants comprising the provided recombinant DNA constructs.

There are provided some embodiments that include methods of expressing a coding sequence or a functional RNA in a flowering plant comprising: introducing a recombinant DNA construct described above into the plant, wherein the heterologous sequence comprises a coding sequence; growing the plant; and selecting a plant displaying expression of the coding sequence or the functional RNA of the recombinant DNA construct.

Furthermore, some embodiments of the present invention include methods of transgenically altering a marketable flower trait of a flowering plant, comprising: introducing a recombinant DNA construct described above into the flowering plant; growing a fertile, mature flowering plant resulting from the introducing step; and selecting a flowering plant expressing the heterologous nucleotide sequence in flower tissue based on the altered marketable flower trait.

Another aspect is for an isolated polynucleotide comprising: (a) a nucleotide sequence encoding a polypeptide, wherein the polypeptide has at least 80% sequence identity, based on the Clustal method of alignment, when compared to the sequence set forth in SEQ ID NO:15, or (b) a full-length complement of the nucleotide sequence of (a).

A further aspect is for an isolated polypeptide, wherein the isolated polypeptide has at least 80% sequence identity, based on the Clustal method of alignment, when compared to the sequence set forth in SEQ ID NO:15.

BRIEF DESCRIPTION OF THE DRAWINGS AND SEQUENCES

The invention can be more fully understood from the following detailed description, the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO:1 is a DNA sequence comprising a 508 bp (base pairs of nucleotides) soybean LTP4 promoter.

SEQ ID NO:2 is an MPSS tag sequence that is specific to the unique gene PSO311306.

SEQ ID NO:3 is a sense primer PSO311306F used in quantitative RT-PCR analysis of PSO311306 gene expression profile.

SEQ ID NO:4 is an antisense primer PSO311306R used in quantitative RT-PCR analysis of PSO311306 gene expression profile.

SEQ ID NO:5 is a sense primer ATPS-87F used as an endogenous control ATP sulfurylase gene-specific primer in the quantitative RT-PCR analysis of PSO311306 gene expression profile.

SEQ ID NO:6 is an antisense primer ATPS-161 R used as an endogenous control ATP sulfurylase gene-specific primer in the quantitative RT-PCR analysis of PSO311306 gene expression profile.

SEQ ID NO:7 is an oligonucleotide primer SAMS-L used in the diagnostic PCR to check for soybean genomic DNA presence in total RNA or cDNA when paired with SEQ ID NO:8.

SEQ ID NO:8 is an oligonucleotide primer SAMS-L2 used in the diagnostic PCR to check for soybean genomic DNA presence in total RNA or cDNA when paired with SEQ ID NO:7.

SEQ ID NO:9 is the longer strand sequence of the adaptor supplied in ClonTech™ GenomeWalker™ kit.

SEQ ID NO:10 is an oligonucleotide primer PSO311306A1 specific to the soybean PSO311306 gene used in the first nested PCR amplification of the LTP4 promoter when paired with SEQ ID NO:11.

SEQ ID NO:11 is an oligonucleotide primer AP1 used in the first nested PCR amplification of the LTP4 promoter when paired with SEQ ID NO:10.

SEQ ID NO:12 is an oligonucleotide primer PSO311306A2 specific to the soybean PSO311306 gene used in the second nested PCR amplification of the LTP4 promoter when paired with SEQ ID NO:13. An NcoI restriction site CCATGG is added for subsequent cloning.

SEQ ID NO:13 is an oligonucleotide primer AP2 used in the second nested PCR amplification of the LTP4 promoter when paired with SEQ ID NO:12.

SEQ ID NO:14 is the 669 bp nucleotide sequence of a novel soybean cDNA PSO311306 encoding a polypeptide with similarity to lipid transfer proteins. Nucleotides 1 to 55 are the 5' untranslated sequence, nucleotides 56 to 58 are the translation initiation codon, nucleotides 56 to 403 are polypeptide coding region, nucleotides 404 to 406 are the termination codon, nucleotides 404 to 669 are the 3' untranslated sequence.

SEQ ID NO:15 is the 116 amino acid long putative PSO311306 translation product LTP4 protein sequence.

SEQ ID NO:16 is a sense primer SAMS-48F used in quantitative PCR analysis of SAMS:ALS transgene copy numbers.

SEQ ID NO:17 is a FAM labeled fluorescent DNA oligo probe SAMS-88T used in quantitative PCR analysis of SAMS:ALS transgene copy numbers.

SEQ ID NO:18 is an antisense primer SAMS-134R used in quantitative PCR analysis of SAMS:ALS transgene copy numbers.

SEQ ID NO:19 is a sense primer YFP-67F used in quantitative PCR analysis of GM-LTP4:YFP transgene copy numbers.

SEQ ID NO:20 is a FAM labeled fluorescent DNA oligo probe YFP-88T used in quantitative PCR analysis of GM-LTP4:YFP transgene copy numbers.

SEQ ID NO:21 is an antisense primer YFP-130R used in quantitative PCR analysis of GM-LTP4:YFP transgene copy numbers.

SEQ ID NO:22 is a sense primer used as an endogenous control heat shock protein gene primer HSP-F1 in quantitative PCR analysis of transgene copy numbers.

SEQ ID NO:23 is a VIC labeled fluorescent DNA oligo probe used as an endogenous control heat shock protein gene probe HSP in quantitative PCR analysis of transgene copy numbers.

SEQ ID NO:24 is an antisense primer used as an endogenous control gene heat shock protein primer HSP-R1 in quantitative PCR analysis of transgene copy numbers.

SEQ ID NO:25 is the 3792 bp sequence of QC372.

SEQ ID NO:26 is the 8317 bp sequence of QC384.

SEQ ID NO:27 is the 8409 bp sequence of QC324i.

SEQ ID NO:28 is the recombination site attL1 sequence in the Gateway cloning system (Invitrogen™).

SEQ ID NO:29 is the recombination site attL2 sequence in the Gateway cloning system (Invitrogen™).

SEQ ID NO:30 is the recombination site attR1 sequence in the Gateway cloning system (Invitrogen™).

SEQ ID NO:31 is the recombination site attR2 sequence in the Gateway cloning system (Invitrogen™).

SEQ ID NO:32 is the recombination site attB1 sequence in the Gateway cloning system (Invitrogen™).

SEQ ID NO:33 is the recombination site attB2 sequence in the Gateway cloning system (Invitrogen™).

FIG. 1 displays the logarithm of relative quantifications of the PSO311306 gene expression in 14 different soybean tissues by quantitative RT-PCR. The gene expression profile indicates that the PSO311306 gene is highly expressed in flower buds and open flowers.

Figure 2:
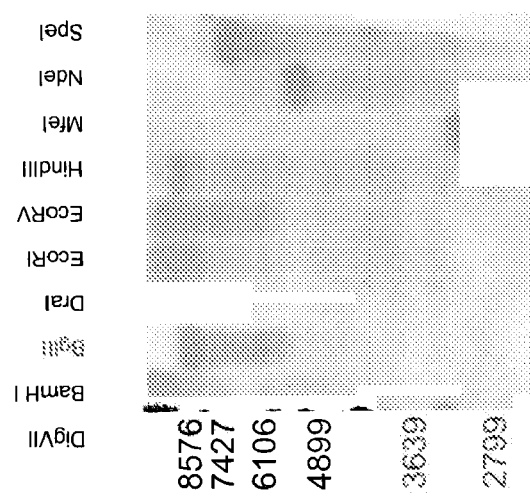

FIG. 2 displays the LTP4 promoter copy number analysis by Southern hybridization.

Figure 3:

FIG. 3 is a schematic representation of the map of plasmid QC372, QC3324i, and QC384.

Figure 4:
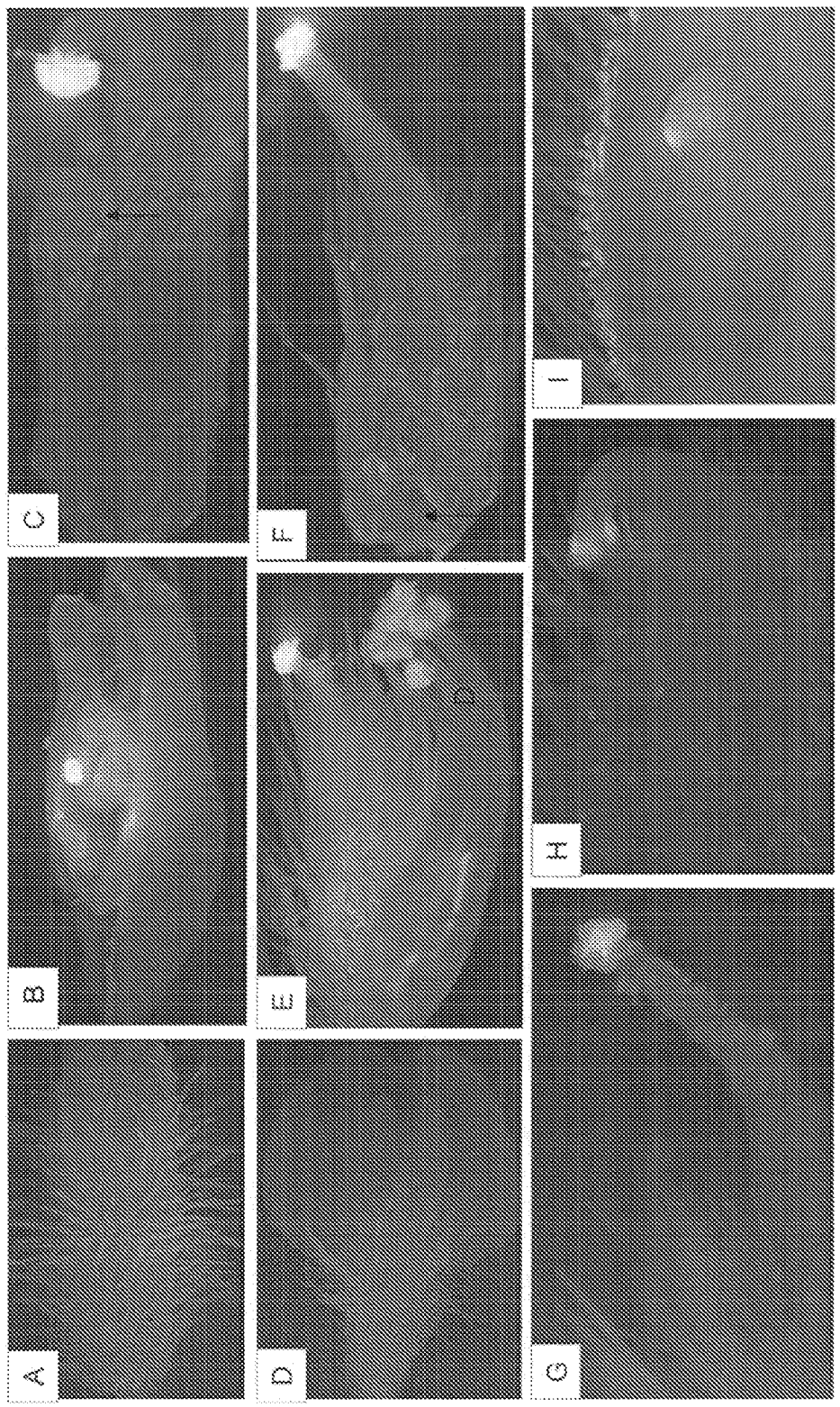

FIG. 4 displays a stable expression of the fluorescent protein reporter gene ZS-YELLOW1 N1 in the floral and other tissues of transgenic soybean plants containing a single copy of the transgene construct QC303. White indicates ZS-YELLOW1 N1 gene expression. Grey is background auto fluorescence from plant green tissues.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

The term "promoter" refers to a nucleotide sequence capable of controlling the expression of a coding sequence or functional RNA. Functional RNA includes, but is not limited to, transfer RNA (tRNA) and ribosomal RNA (rRNA). Numerous examples of promoters may be found in the compilation by Okamuro and Goldberg (Biochemistry of Plants 15:1-82 (1989)). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that, since in most cases the exact boundaries of regulatory sequences have not been completely defined, DNA fragments of some variation may have identical promoter activity.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

A "flower" is a complex structure consisting of pedicel, sepal, petal, stamen, and carpel. A stamen comprises an anther, pollen and filament. A carpel comprises a stigma, style and ovary. An ovary comprises an ovule, embryo sac, and egg cell. Soybean pods develop from the pistil. It is likely that a gene expressed in the pistil of a flower continues to express in early pod. A "flower cell" is a cell from any one of these structures. Flower promoters in general include promoters that direct gene expression in any of the above tissues or cell types.

The term "flower crop" or "flowering plants" are plants that produce flowers that are marketable within the floriculture industry. Flower crops include both cut flowers and potted flowering plants. Cut flowers are plants that generate flowers that can be cut from the plant and can be used in fresh flower arrangements. Flower crops include roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

The terms "flower-specific promoter" or "flower-preferred promoter" may be used interchangeably herein and refer to promoters active in flower, with promoter activity being significantly higher in flower tissue versus non-flower tissue. "Preferentially initiates transcription", when describing a particular cell type, refers to the relative level of transcription in that particular cell type as opposed to other cell types. The described LTP4 promoter is a promoter that preferentially initiates transcription in flower cells. Preferably, the promoter activity in terms of expression levels of an operably linked sequence is more than ten-fold higher in flower tissue than non-flower tissue. More preferably, the promoter activity is present in flower tissue while undetectable in non-flower tissue.

As used herein, an "LTP4 promoter" refers to one type of flower-specific promoter. The native LTP4 promoter (or full-length native LTP4 promoter) is the native promoter of the putative soybean LTP4 polypeptide, which is a novel soybean protein with homology to many lipid transfer proteins identified in other species (see, e.g., Parida and George, Genome 50:470-478 (2007); Jaillon et al., Nature 449:463-467 (2007); Finkina et al., Biokhimiia 72:430-438 (2007)). The "LTP4 promoter", as used herein, also refers to fragments of the full-length native promoter that retain significant promoter activity. For example, an LTP4 promoter of the present invention can be the full-length promoter (SEQ ID NO:1) or a promoter-functioning fragment thereof. An LTP4 promoter also includes variants that are substantially similar and functionally equivalent to any portion of the nucleotide sequence set forth in SEQ ID NO:1.

An "isolated nucleic acid fragment" or "isolated polynucleotide" refers to a polymer of ribonucleotides (RNA) or deoxyribonucleotides (DNA) that is single-stranded or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" or "heterologous nucleotide sequence" refers to a nucleotide sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoter may be used with their native coding sequences to increase or decrease expression resulting in a change in phenotype in the transformed seed.

The terms "fragment (or variant) that is functionally equivalent" and "functionally equivalent fragment (or variant)" are used interchangeably herein. These terms refer to a portion or subsequence or variant of the promoter sequence of the present invention in which the ability to initiate transcription or drive gene expression (such as to produce a certain phenotype) is retained. Fragments and variants can be obtained via methods such as site-directed mutagenesis and synthetic construction. As with the provided promoter sequences described herein, the contemplated fragments and variants operate to promote the flower-preferred expression of an operably linked heterologous nucleic acid sequence, forming a recombinant DNA construct (also, a chimeric gene). For example, the fragment or variant can be used in the design of recombinant DNA constructs to produce the desired phenotype in a transformed plant. Recombinant DNA constructs can be designed for use in co-suppression or antisense by linking a promoter fragment or variant thereof in the appropriate orientation relative to a heterologous nucleotide sequence.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides of SEQ ID NO:1. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "substantially similar" and "corresponding substantially" as used herein refer to nucleic acid sequences, particularly promoter sequences, wherein changes in one or more nucleotide bases do not substantially alter the ability of the promoter to initiate transcription or drive gene expression or produce a certain phenotype. These terms also refer to modifications, including deletions and variants, of the nucleic acid sequences of the instant invention by way of deletion or insertion of one or more nucleotides that do not substantially alter the functional properties of the resulting promoter relative to the initial, unmodified promoter. It is therefore understood, as those skilled in the art will appreciate, that the invention encompasses more than the specific exemplary sequence.

In one example of substantially similar, substantially similar nucleic acid sequences include those that are also defined by their ability to hybridize to the disclosed nucleic acid sequences, or portions thereof. Substantially similar nucleic acid sequences include those sequences that hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2× SSC, 0.5% SDS is increased to 60° C. Another set of highly stringent conditions uses two final washes in 0.1×SSC, 0.1% SDS at 65° C.

In some examples, substantially similar nucleic acid sequences are those sequences that are at least 80% identical to the nucleic acid sequences reported herein or which are at least 80% identical to any portion of the nucleotide sequences reported herein. In some instances, substantially similar nucleic acid sequences are those that are at least 90% identical to the nucleic acid sequences reported herein, or at least 90% identical to any portion of the nucleotide sequences reported herein. In some examples, substantially similar nucleic acid sequences are those that are at least 95% identical to the nucleic acid sequences reported herein, or are at least 95% identical to any portion of the nucleotide sequences reported herein. It is well understood by one skilled in the art that many levels of sequence identity are useful in identifying related polynucleotide sequences. Useful examples of percent identities are those listed above, or also any integer percentage from 80% to 100%, such as, for example, 81%, 82%, 83%, 84%, 85%, 86%, 87%, 88%, 89%, 90%, 91%, 92%, 93%, 94%, 95%, 96%, 97%, 98% and 99%.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid sequence for improved expression in a host cell, it is desirable to design the nucleic acid sequence such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WIN- DOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, and arranged in a manner different than that found in nature. "Endogenous gene" refers to a native gene in its natural location in the genome of an organism. A "foreign" gene refers to a gene not normally found in the host organism, which is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that encodes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, and are not limited to, promoters, enhancers, translation leader sequences, introns, and polyadenylation recognition sequences.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized as affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript, or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated yet has an effect on cellular processes.

The term "operably linked" refers to the association of nucleic acid sequences on a single polynucleotide so that the function of one is affected by the other. For example, a promoter is operably linked with a heterologous nucleotide sequence, e.g., a coding sequence, when it is capable of affecting the expression of that heterologous nucleotide sequence (i.e., for example, the coding sequence is under the transcriptional control of the promoter). A coding sequence can be operably linked to promoter sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product, e.g., an mRNA or a protein (precursor or mature).

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication Nos. WO99/53050 and WO02/00904). This increases the frequency of co-suppression in the recovered transgenic plants. Another variation describes the use of plant viral sequences to direct the suppression, or "silencing", of proximal mRNA encoding sequences (PCT Publication No. WO98/36083). Neither of these co-suppressing phenomena has been elucidated mechanistically at the molecular level, although genetic evidence has been obtained that may lead to the identification of potential components (Elmayan et al., Plant Cell 10:1747-1757 (1998)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. Thus, a "transgenic plant cell" as used herein refers to a plant cell containing the transformed nucleic acid fragments. The preferred method of soybean cell transformation is use of particle-accelerated or "gene gun" transformation technology (Klein et al., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

A "marketable flower trait" is a characteristic or phenotype of the flower of a plant such as the color, scent or morphology of a flower. The marketable flower trait is a characteristic of a flower that is of high regard to a flower crop consumer in deciding whether to purchase the flower crop.

The phrase "genes involved in anthocyanin biosynthesis" refers to genes that encode proteins that play a role in converting metabolic precursors into the one of a number of anthocyanins. Examples of genes involved in the biosynthesis of anthocyanin are dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase (see, e.g., Mori et al., Plant Cell Reports 22:415-421 (2004)).

The phrase "genes involved in the biosynthesis of fragrant fatty acid derivatives" refers to genes that encode proteins that play a role in manipulating the biosynthesis of fragrant fatty acid derivatives such as terpenoids, phenylpropanoids, and benzenoids in flowers (see, e.g., Tanaka et al., Plant Cell, Tissue and Organ Culture 80:1-24 (2005)). Examples of such genes include S-linalool synthase, acetyl CoA:benzylalcohol acetyltransferase, benzyl CoA:benzylalcohol benzoyl transferase, S-adenosyl-L-methionine:benzoic acid carboxyl methyl transferase (BAMT), mycrene synthases, (E)-β-ocimene synthase, orcinol O-methyltransferase, and limonene synthases (see, e.g., Tanaka et al., supra).

The term "flower homeotic genes" or "flower morphology modifying genes" refers to genes that are involved in pathways associated with flower morphology. A modification of flower morphology can lead to a novel form of the respective flower that can enhance its value in the flower crop marketplace. Morphology can include the size, shape, or petal pattern of a flower. Some example of flower homeotic genes include genes involved in cell-fate determination (in ABC combinatorial model of gene expression), including AGAMOUS, which determines carpel fate in the central whorl, APETALA3, which determines the sepal fate in the outer whorl, and PISTILLATA, which determines petal development in the second whorl (Espinosa-Soto et al., *Plant Cell* 16:2923-2939 (2004)).

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments consisting of a series of repetitive cycles (Perkin Elmer Cetus Instruments, Norwalk, Conn.). Typically, the double stranded DNA is heat denatured; the two primers complementary to the 3' boundaries of the target segment are annealed at low temperature and then extended at an intermediate temperature. One set of these three consecutive steps comprises a cycle.

Embodiments of the present invention include isolated polynucleotides comprising a nucleotide sequence that is a promoter. In some instances the nucleotide sequence includes one or more of the following:

a) the sequence set forth in SEQ ID NO:1 or a full-length complement thereof; or b) a nucleotide sequence comprising a sequence having at least 90% sequence identity, based on the BLASTN method of alignment, when compared to the sequence set forth in SEQ ID NO:1.

In other aspects, the nucleotide sequence includes one or more of the following:

(a) a nucleotide sequence comprising a fragment of SEQ ID NO:1, or (b) a nucleotide sequence comprising a sequence having at least 90% sequence identity, based on the BLASTN method of alignment, when compared to the nucleotide sequence of (a).

The nucleotide sequences of the present invention can be referred to as a promoter or as having promoter-like activity. In some embodiments the nucleotide sequence is a promoter that preferentially initiates transcription in a plant flower cell. Such promoter is referred to as a flower-specific promoter. Preferably the promoter of the present invention is the soybean "LTP4" promoter. The LTP4 promoter of the invention expresses in stigma, therefore the promoter may be used to express genes involved in pollination compatibility.

In a preferred embodiment, the promoter comprises the nucleotide sequence set forth in SEQ ID NO:1. The present invention also includes nucleic acid fragments, variants, and complements of the aforementioned nucleotide sequences or promoters, provided that they are substantially similar and functionally equivalent to the nucleotide sequence set forth in these nucleotide sequences. A nucleic acid fragment or variant that is functionally equivalent to the present LTP4 promoter is any nucleic acid fragment or variant that is capable of initiating the expression, preferably initiating flower-specific expression, of a coding sequence or functional RNA in a similar manner to the LTP4 promoter. The expression patterns of LTP4 gene and its promoter are set forth in Examples 1, 2, and 6.

In some aspects, a recombinant DNA construct can be formed in part by operably linking at least one of the promoters of the present invention to any heterologous nucleotide sequence. The heterologous nucleotide sequence can be expressed in a cell as either a functional RNA or a polypeptide. The cell for expression includes a plant or bacterial cell, preferably a plant cell. The recombinant DNA construct preferably includes the LTP4 promoter. The recombinant DNA construct preferably includes a heterologous nucleotide sequence that encodes a protein that plays a role in flower color formation, fragrance production, or shape/morphology development of the flower. The color of a flower can be altered transgenically by expressing genes involved in betalain, carotenoid, or flavanoid biosynthesis. In regard to genes involved in the biosynthesis of anthocyanin, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase are some examples. The scent of a flower can be altered transgenically by expressing genes that manipulate the biosynthesis of fragrant fatty acid derivatives such as terpenoids, phenylpropanoids, and benzenoids in flowers. Some embodiments of the invention include a heterologous nucleotide sequence that is selected from S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthases, (E)-β-ocimene synthase, orcinol O-methyltransferase, or limonene synthases. Flower structures/morphologies can be altered transgenically by expressing flower homeotic genes to create novel ornamental varieties. Some embodiments of the invention include a heterologous nucleotide sequence that is selected from genes such as, for example, AGAMOUS, APETALA3, and PISTILLATA.

It is recognized that the instant promoters may be used with their native coding sequences to increase or decrease expression in flower tissue. The selection of the heterologous nucleic acid fragment depends upon the desired application or phenotype to be achieved. The various nucleic acid sequences can be manipulated so as to provide for the nucleic acid sequences in the proper orientation.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the recombinant DNA construct.

The described polynucleotide embodiments encompass isolated or substantially purified nucleic acid compositions. An "isolated" or "purified" nucleic acid molecule, or biologically active portion thereof, is substantially free of other cellular material or culture medium when produced by recombinant techniques, or substantially free of chemical precursors or other chemicals when chemically synthesized. An "isolated" nucleic acid is essentially free of sequences (preferably protein encoding sequences) that naturally flank the polynucleotide (i.e., sequences located at the 5' and 3' ends of the nucleic acid) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide is derived.

In another embodiment, the present invention includes host cells comprising either the recombinant DNA constructs or isolated polynucleotides of the present invention. Examples of the host cells of the present invention include, and are not limited to, yeast, bacteria, and plants, including flower crops such as, e.g., rose, carnation, *Gerbera, Chrysanthemum*, tulip, *Gladioli, Alstroemeria, Anthurium*, lisianthus, larkspur, irises, orchid, snapdragon, African violet, or azalea. Preferably, the host cells are plant cells, and more preferably, flower crop cells, and more preferably, *Gerbera*, rose, carnation, *Chrysanthemum*, or tulip cells.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); Brassica (U.S. Pat. No. 5,463,174); peanut (Cheng et al., Plant Cell Rep. 15:653-657 (1996); McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection (Neuhaus et al., Physiol. Plant. 79:213-217 (1990)), or particle bombardment (McCabe et al., Biotechnology 6:923 (1988); Christou et al., Plant Physiol. 87:671-674 (1988)).

In another embodiment, the present invention includes transgenic plants comprising the recombinant DNA constructs provided herein. The transgenic plants are selected from, for example, one of a number of various flower crops including roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

In some embodiments of the invention, there are provided transgenic seeds produced by the transgenic plants provided. Such seeds are able to produce another generation of transgenic plants.

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, there are generally available standard resource materials that describe specific conditions and procedures for the construction, manipulation and isolation of macromolecules (e.g., DNA molecules, plasmids, and the like), generation of recombinant DNA fragments and recombinant expression constructs, and the screening and isolating of clones (see, for example, Sambrook et al., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by northern analysis of mRNA expression, western analysis of protein expression, or phenotypic analysis. Also of interest are seeds obtained from transformed plants displaying the desired expression profile.

The level of activity of the LTP4 promoter in flowers is in some cases comparable to that of many known strong promoters such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis* oleosin promoters (Plant et al., Plant Mol. Biol. 25:193-205 (1994); Li, Texas A&M University Ph.D. dissertation, pp. 107-128 (1997)), the *Arabidopsis* ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter (Raschke et al., J. Mol. Biol. 199(4):549-557 (1988)), and a maize H3 histone gene promoter (Atanassova et al., Plant Mol. Biol. 37:275-285 (1998)).

In some embodiments, the promoters of the present invention are useful when flower-specific expression of a target heterologous nucleic acid fragment is required. Another useful feature of the promoters is its expression profile having high levels in developing stigmas (See Example 6). The promoters of the present invention are most active in the stigmas of developing flower buds and open flowers. Thus, the promoters can be used for gene expression or gene silencing in flowers, especially when gene expression or gene silencing is desired predominantly in stigmas.

In some embodiments, the promoters of the present invention are to construct recombinant DNA constructs that can be used to reduce expression of at least one heterologous nucleic acid sequence in a plant cell. To accomplish this, a recombinant DNA construct can be constructed by linking the heterologous nucleic acid sequence to a promoter of the present invention. (See U.S. Pat. No. 5,231,020 and PCT Publications WO99/53050, WO02/00904, and WO98/36083 for methodology to block plant gene expression via cosuppression) Alternatively, recombinant DNA constructs designed to express antisense RNA for a heterologous nucleic acid fragment can be constructed by linking the fragment in reverse orientation to a promoter of the present invention. (See U.S. Pat. No. 5,107,065 for methodology to block plant gene expression via antisense RNA) Either the cosuppression or antisense chimeric gene can be introduced into plants via transformation. Transformants, wherein expression of the heterologous nucleic acid sequence is decreased or eliminated, are then selected.

There are embodiments of the present invention that include promoters of the present invention being utilized for methods of altering (increasing or decreasing) the expression of at least one heterologous nucleic acid sequence in a plant cell which comprises: transforming a plant cell with a recombinant DNA expression construct described herein; growing fertile mature plants from the transformed plant cell; and selecting plants containing a transformed plant cell wherein the expression of the heterologous nucleotide sequence is altered (increased or decreased).

Transformation and selection can be accomplished using methods well-known to those skilled in the art including, but not limited to, the methods described herein.

There are provided some embodiments that include methods of expressing a coding sequence in a plant that is a flower crop comprising: introducing a recombinant DNA construct disclosed herein into the plant; growing the plant; and selecting a plant displaying expression of the coding sequence; wherein the nucleotide sequence comprises: a nucleotide sequence comprising the sequence set forth in SEQ ID NO:1 or a full-length complement thereof; a nucleotide sequence comprising a fragment of the sequence set forth in SEQ ID NO:1, or a nucleotide sequence comprising a sequence having at least 90% sequence identity, based on the BLASTN method of alignment, when compared to the sequence set forth in SEQ ID NO:1; wherein said nucleotide sequence initiates transcription in a flower cell of the plant.

Furthermore, some embodiments of the present invention include methods of transgenically altering a marketable flower trait of a flowering plant, comprising: introducing a recombinant DNA construct disclosed herein into the flowering plant; growing a fertile, mature flowering plant resulting from the introducing step; and selecting a flowering plant expressing the heterologous nucleotide sequence in flower tissue based on the altered marketable flower trait.

As further described in the Examples below, the promoter activity of the soybean genomic DNA fragment sequence SEQ ID NO:1 upstream of the LTP4 protein coding sequence was assessed by linking the fragment to a yellow fluorescence reporter gene, ZS-YELLOW1 N1 (YFP) (Matz et al., Nat. Biotechnol. 17:969-973 (1999)), transforming the promoter:: YFP expression cassette into soybean, and analyzing YFP expression in various cell types of the transgenic plants (see Example 6). All parts of the transgenic plants were analyzed and YFP expression was predominantly detected in flowers, and more specifically in stigmas. These results indicated that the nucleic acid fragment contained flower-preferred promoter.

Some embodiments of the present invention provide recombinant DNA constructs comprising at least one isopentenyl transferase nucleic acid sequence operably linked to a provide promoter, preferably a LTP4 promoter. The isopentenyl transferase plays a key step in the biosynthesis of plant cytokinin (Kakimoto, J. Plant Res. 116:233-239 (2003)). Elevated levels of cytokinin in plant cells might help to delay floral senescence and abortion which may present a potential way to improve crop yields (Chang et al., Plant Physiol. 132:2174-2183 (2003); Young et al., Plant J. 38:910-922 (2004)).

Utilities for Flower-Specific Promoters

The color, scent or morphology of a flower represents marketable flower traits, or characteristics/phenotypes of a flower that consumers, particularly floriculturalists, consider when determining which flowers are desirable and will be purchased. Hence, it would be beneficial to be able to alter these characteristics in order to satisfy the desires of consumers. Transgenic technologies can be implemented in order to achieve such results.

The phenotype of a flower can be altered transgenically by expressing genes, preferably in flower tissue, that play a role in color formation, fragrance production, or shape/morphology development of the flower. This type of alteration is particularly useful in the floriculture industry, and particularly useful for flowering plants.

The color of a flower is mainly the result of three types of pigment, flavanoids, carotenoids, and betalains. The flavanoids are the most common of the three and they contribute to colors ranging from yellow to red to blue, with anthocyanins being the major flavanoid. Carotenoids are C-40 tetraterpenoids that contribute to the majority of yellow hues and contribute to orange/red, bronze and brown colors, e.g., that seen in roses and chrysanthemums. Betalains are the least abundant and contribute to various hues of ivory, yellow, orange, red and violet. The color of a flower can be altered transgenically by expressing genes involved in, e.g., betalain, carotenoid, or flavanoid biosynthesis. In one example, the color of a flower can be altered transgenically by expressing genes involved in the biosynthesis of anthocyanin, for example, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase. In some aspects of the invention, the gene involved in anthocyanin biosynthesis is the flavonoid 3,5-hydroxylase gene (see, e.g., Mori et al., Plant Cell Reports 22:415-421 (2004)). This type of alteration is particularly useful in the floriculture industry, providing novel flower colors in flower crops.

In addition to color, the scent of a flower can be altered transgenically by expressing genes that manipulate the biosynthesis of fragrant fatty acid derivatives such as terpenoids, phenylpropanoids, and benzenoids in flowers (see, e.g., Tanaka et al., Plant Cell, Tissue and Organ Culture 80:1-24 (2005)). Genes involved in the biosynthesis of fragrant fatty acid derivatives can be operably linked to the flower-specific promoters presently described for preferential expression in flower tissue. The preferential expression in flower tissue can be utilized to generate new and desirable fragrances to enhance the demand for the underlying cut flower. A number of known genes that are involved in the biosynthesis of floral scents are described below. A strong sweet scent can be generated in a flower by introducing or up-regulating expression of S-linalool synthase, which was earlier isolated from *Clarkia breweri*. Two genes that are responsible for the production of benzylacetate and benzylbenzoate are acetyl CoA:benzylalcohol acetyltransferase and benzyl CoA:benzylalcohol benzoyl transferase, respectively. These transferases were also reported to have been isolated from *C. breweri*. A phenylpropanoid floral scent, methylbenzoate, is synthesized in part by S-adenosyl-L-methionine:benzoic acid carboxyl methyl transferase (BAMT), which catalyzes the final step in the biosynthesis of methyl benzoate. BAMT is known to have a significant role in the emission of methyl benzoate in snapdragon flowers. Two monoterpenes, mycrene and (E)-β-ocimene, from snapdragon are known to be synthesized in part by the terpene synthases: mycrene synthases and (E)-β-ocimene synthases. Other genes involved in biosynthesis of floral scents have been reported and are being newly discovered, many of which are isolated from rose. Some genes involved in scent production in the rose include orcinol O-methyltransferase, for synthesis of S-adenosylmethionine, and limonene synthases (see, e.g., Tanaka et al., supra).

Flower structures/morphologies can be altered transgenically by expressing flower homeotic genes to create novel ornamental varieties. The flower homeotic genes that are determinative of flower morphology include genes such as AGAMOUS, APETALA3, PISTILLATA, and others that are known and/or are being elucidated (see, e.g., Espinosa-Soto et al., Plant Cell 16:2923-2939 (2004)).

EXAMPLES

Aspects of the present invention are exemplified in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

In the discussion below, parts and percentages are by weight and degrees are Celsius, unless otherwise stated. Sequences of promoters, cDNA, adaptors, and primers listed herein are in the 5' to 3' orientation unless described otherwise. Techniques in molecular biology were typically performed as described in Ausubel et al., 1990 or Sambrook et al., 1989.

Example 1

Lynx MPSS Profiling of Soybean Genes Preferably Expressed in Flowers

Soybean expression sequence tags (ESTs) were generated by sequencing randomly selected clones from cDNA libraries constructed from different soybean tissues. Multiple EST sequences may have different lengths representing different regions of the same soybean gene. For those EST sequences representing the same gene that are found more frequently in a flower-specific cDNA library, there is a possibility that the representative gene could be a flower preferred gene candidate. Multiple EST sequences representing the same soybean gene were compiled electronically based on their overlapping sequence homology into a full length sequence representing a unique gene. These assembled, unique gene sequences were cumulatively collected and the information was stored in a searchable database. Flower specific candidate genes were identified by searching this database to find gene sequences that are frequently found in flower libraries but are rarely found in other tissue libraries, or not found in other tissue libraries.

One unique gene, PSO311306, was identified in the search as a flower specific gene candidate since all of the ESTs representing PSO311306 were mostly found in flower tissue. PSO311306 cDNA sequence (SEQ ID NO:14) as well as its putative translated protein sequence (SEQ ID NO:15) were used to search National Center for Biotechnology Information (NCBI) databases. PSO311306 was found to represent a novel soybean gene with significant homology to lipid transfer protein genes identified in different species (e.g., over 50% identity to lipid transfer proteins from, e.g., *Retama raetam* (white weepin broom), *Prosopis juliflora* (Mesquite), *Vitis vinifera* (European grapevine), *Davidia involucratav* (dove tree), *Prunus avium* (sweet cherry), *Populus alba*× *Populus tremula* var. *glandulosa* (poplar), *Prunus persica* (peach), *Vigna radiate* (mung bean)). PSO311306 was subsequently named LTP4 to reflect this sequence homology.

A more sensitive gene expression profiling methodology MPSS (Mass Parallel Signature Sequence) transcript profiling technique (Brenner et al., Proc Natl Acad Sci USA 97:1665-70 (2000)) was used to confirm PSO311306 as a flower specific gene. The MPSS technology involves the generation of 17 base signature tags from mRNA samples that have been reverse transcribed from poly A+ RNA isolated using standard molecular biology techniques (Sambrook et al., 1989). The tags are simultaneously sequenced and assigned to genes or ESTs. The abundance of these tags is given a number value that is normalized to parts per million (PPM) which then allows the tag expression, or tag abundance, to be compared across different tissues. Genome wide gene expressions can be profiled simultaneously using this technology. Since each 17 base tag is long enough to be specific to only one or a few genes in any genome, the MPSS platform can be used to determine the expression pattern of a particular gene and its expression levels in different tissues.

MPSS gene expression profiles were generated from different soybean tissues over time, and the profiles were accumulated in a searchable database. PSO311306 cDNA sequence SEQ ID NO:14 was used to search the MPSS database to identify a MPSS tag sequence (SEQ ID NO:2) that is identical to a 17 base pair region from position 375 to 391 at the end of PSO311306 polypeptide coding region. The identified MPSS tag was then used to search the MPSS database to reveal its abundance in different soybean tissues. As illustrated in Table 1, the PSO311306 gene was confirmed to be highly abundant in flowers and also detectable in leaf, pod, and petiole, a desired expression profile for its promoter to be able to express genes in flowers.

TABLE 1

Lynx MPSS Expression Profiles of the PSO311306 Gene

| Target gene | PSO311306 |
|---|---|
| Tag sequence | SEQ ID NO: 2 |
| Flower | 7556 |
| Pod | 201 |
| Flower bud | 10064 |
| Lateral root | 0 |
| Leaf | 445 |
| Petiole | 160 |
| Primary root | 0 |
| Seed | 0 |
| Stem | 12 |

Example 2

Quantitative RT-PCR Profiles of LTP4 Gene Expression in Soybean

The MPSS profiles of LTP4 gene, i.e. PSO311306, was confirmed and extended by analyzing 14 different soybean tissues using the relative quantitative RT-PCR (qRT-PCR) technique with a 7500 real time PCR system (Applied Biosystems, Foster City, Calif.).

Fourteen soybean tissues (somatic embryo in suspension culture, somatic embryo grown one week on solid medium, leaf, leaf petiole, root, flower bud, open flower, R3 pod, R4 seed, R4 pod coat, R5 seed, R5 pod coat, R6 seed, R6 pod coat) were collected from cultivar 'Jack' and flash frozen in liquid nitrogen. The seed and pod development stages were defined according to descriptions in Fehr and Caviness, IWSRBC 80:1-12 (1977). Total RNA was extracted with Trizol reagents (Invitrogen™, Carlsbad, Calif.) and treated with DNase I to remove any trace amount of genomic DNA contamination. The first strand cDNA was synthesized with Superscript III reverse transcriptase (Invitrogen™).

PCR analysis was performed to confirm that the cDNA was free of genomic DNA. The forward and reverse primers used for the PCR analysis are shown in SEQ ID NO:7 and SEQ ID NO:8. The primers are specific to the 5'UTR intron/exon junction region of a soybean S-adenosylmethionine synthetase (SAMS) gene promoter (PCT Publication No. WO0/37662). PCR using this primer set will amplify a 967 bp DNA fragment from a soybean genomic DNA template and a 376 bp DNA fragment from the cDNA template. The genomic DNA-free cDNA aliquots were used in qRT-PCR analysis of PSO311306 using gene-specific primers SEQ ID NO:3 and SEQ ID NO:4. An endogenous soybean ATP sulfurylase gene was used as an internal control for normalization with primers SEQ ID NO:5 and SEQ ID NO:6 and soybean wild type genomic DNA was used as the calibrator for relative quantification.

The qRT-PCR profiling of the LTP4 gene expression confirmed its predominant flower expression and also showed ongoing expression in young R3 pod and R4 pod coat (FIG. 1).

Example 3

Isolation of Soybean LTP4 Promoter

The soybean genomic DNA fragment corresponding to the LTP4 promoter was isolated using a polymerase chain reaction (PCR) based approach called genome walking using the Universal GenomeWalker™ kit from Clontech™ (Product User Manual No. PT3042-1).

Soybean genomic DNA samples were digested, separately, to completion with four restriction enzymes DraI, EcoRV, HpaI, or PmlI, each of which generates DNA fragments having blunt ends. Double strand adaptors (SEQ ID NO:9) supplied in the GenomeWalker™ kit were added to the blunt ends of the genomic DNA fragments by DNA ligase. Two rounds of PCR were performed to amplify the LTP4 corresponding genomic DNA fragment using two nested primers supplied in the Universal GenomeWalker™ kit that are specific to the adaptor sequence (AP1 and AP2, for the first and second adaptor primer, respectively), and two LTP4 gene specific primers (GSP1 and GSP2) designed based on the 5' coding sequence of LTP4 (PSO311306). The oligonucleotide sequences of the four primers are shown in SEQ ID NO:10 (GSP1), SEQ ID NO:11 (AP1), SEQ ID NO:12 (GSP2), and in SEQ ID NO:13 (AP2). The GSP2 primer contains a recognition site for the restriction enzyme NcoI. The AP2 primer from the Universal GenomeWalker™ kit contains a SalI restriction site. The 3' end of the adaptor sequence SEQ ID NO:9 contains a XmaI recognition site downstream to the corresponding SalI restriction site in AP2 primer.

The AP1 and the GSP1 primers were used in the first round PCR using each of the adaptor ligated genomic DNA samples (DraI, EcoRV, HpaI or PmlI) under conditions defined in the GenomeWalker™ protocol. Cycle conditions were 94° C. for 4 minutes; 35 cycles of 94° C. for 30 seconds, 60° C. for 1 minute, and 68° C. for 3 minutes; and a final 68° C. for 5 minutes before holding at 4° C. One microliter from each of the first round PCR products was used as templates for the second round PCR with the AP2 and GSP2 primers. Cycle conditions for second round PCR were 94° C. for 4 minutes; 25 cycles of 94° C. for 30 seconds, 60° C. for 1 minute, and 68° C. for 3 minutes; and a final 68° C. for 5 minutes before holding at 4° C. Agarose gels were run to identify specific PCR product with an optimal fragment length. An approximately 0.6 Kb PCR product was detected and subsequently cloned into pCR2.1-TOPO vector by TOPO TA cloning (Invitrogen™). Sequencing of the cloned PCR products revealed that its 3' end matched the 5' end of the PSO311306 cDNA sequence, indicating that the PCR product was indeed the corresponding LTP4 genomic DNA fragment. The 508 bp genomic DNA sequence upstream of the putative LTP4 start codon ATG is herein designated as soybean LTP4 promoter (SEQ ID NO:1), which includes 8 bp GGGCTGGT non-soybean DNA sequence at the 5' end derived from the DNA adaptor in the GenomeWalker™ kit.

Example 4

LTP4 Promoter Copy Number Analysis

Southern hybridization analysis was performed to determine if there is any other sequence in the soybean genome with high similarity to the LTP4 promoter. Soybean 'Jack' wild type genomic DNA was digested with nine different restriction enzymes BamHI, BglII, DraI, EcoRI, EcoRV, HindIII, MfeI, NdeI, and SpeI, each separately, and distributed in a 0.7% agarose gel by electrophoresis. The DNA was blotted onto a Nylon membrane and hybridized in EasyHyb Southern hybridization solution with digoxigenin (DIG) labeled LTP4 promoter DNA probe, and then sequentially washed 10 minutes with 2×SSC/0.1% SDS at room temperature and 3×10 minutes at 65° C. with 0.1×SSC/0.1% SDS according to the protocol provided by the manufacturer (Roche Applied Science, Indianapolis, Ind.). The LTP4 promoter probe was labeled by PCR using the DIG DNA labeling kit (Roche Applied Science) with primers SEQ ID NO:12 and SEQ ID NO:13 to make a 539 bp DNA fragment including the entire 508 bp LTP4 promoter sequence (SEQ ID NO:1) plus a part of the GenomeWalker™ kit DNA adaptor sequence.

Single band was expected for eight digestions BamHI, BglII, EcoRI, EcoRV, HindIII, MfeI, NdeI, and SpeI if the LTP4 promoter sequence is unique in soybean genome since none of them cut inside the LTP4 probe. As expected, a single band was detected in each of the lanes loaded with DNA digested, respectively, with the above eight restriction enzymes (FIG. 2). Though enzyme DraI would cut LTP4 promoter at position 63 of LTP4 promoter, the 63 bp sequence would be too short to stably hybridize to the probe under the stringent Southern hybridization conditions. Single band was also expected for DraI digestion but no band was indeed observed (FIG. 2). The DraI digestion probably produced a band too small to be retained on the Southern blot which retained only DNA fragments larger than ~1 Kb. In conclusion, there is only one copy of the LTP4 promoter sequence in soybean genome.

Example 5

LTP4:YFP Reporter Constructs and Soybean Transformation

The cloned LTP4 promoter fragment described in EXAMPLE 3 was digested with NcoI and XmaI, gel purified using a DNA gel extraction kit (Qiagen, Valencia, Calif.) and cloned into the NcoI and XmaI sites of a Gateway cloning ready vector QC312 containing the yellow fluorescent reporter gene ZS-YELLOW1 N1 (YFP) to make the reporter construct QC372 (SEQ ID NO:25) with the soybean LTP4 promoter driving the YFP gene expression (FIG. 3). The LTP4:YFP expression cassette in construct QC372 was linked to the SAMS:ALS (S-adenosyl methionine synthetase: acetolactate synthase) expression cassette in construct QC324i (SEQ ID NO:27, FIG. 3) to create construct QC384 (SEQ ID NO:26, FIG. 3) by Gateway cloning using LR clonase (Invitrogen™). The linked LTP4:YFP and SAMS:ALS cassettes were released as a 5803 bp DNA fragment from construct QC384 by AscI restriction digestion, separated from the vector backbone fragment by agarose gel electrophoresis, and purified from the gel using a Qiagen DNA gel extraction kit. The purified DNA fragment was used to transform soybean cultivar Jack using the particle gun bombardment method (Klein et al., Nature 327:70-73 (1987); U.S. Pat. No. 4,945,050) to study the LTP4 promoter activity in stably transformed soybean plants.

Soybean somatic embryos from the Jack cultivar were induced as follows. Cotyledons (smaller than 3 mm in length) were dissected from surface-sterilized, immature seeds and were cultured for 6-10 weeks under fluorescent light at 26° C. on a Murashige and Skoog media ("MS media") containing 0.7% agar and supplemented with 10 mg/ml 2,4-dichlorophenoxyacetic acid (2,4-D). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (helium retrofit) (Bio-Rad Laboratories, Hercules, Calif.). To 50 µl of a 60 mg/ml 1.0 mm gold particle suspension were added (in order): 30 µl of 10 ng/µl LTP4:YFP+SAMS:ALS DNA fragment, 20 µl of 0.1 M spermidine, and 25 µl of 5 M $CaCl_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. 5 µl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to solid agar MS media plates without 2,4-D supplement to allow somatic embryos to develop. A sample of each event was collected at this stage for PCR and quantitative PCR analysis.

Cotyledon stage somatic embryos were dried-down (by transferring them into an empty small Petri dish that was seated on top of a 10 cm Petri dish to allow slow dry down) to mimic the last stages of soybean seed development. Dried-down embryos were placed on germination solid media, and transgenic soybean plantlets were regenerated. The transgenic plants were then transferred to soil and maintained in growth chambers for seed production.

Genomic DNA was extracted from somatic embryo samples and analyzed by quantitative PCR using the 7500 real time PCR system (Applied Biosystems) with gene-specific primers and 6-carboxyfluorescein (FAM)-labeled fluorescence probes to check copy numbers of both the SAMS:ALS expression cassette and the LTP4:YFP expression cassette. The qPCR analysis was done in duplex reactions with a heat shock protein (HSP) gene as the endogenous control and a transgenic DNA sample with a known single copy of SAMS:ALS or YFP transgene as the calibrator using the relative quantification methodology. The endogenous control HSP probe was labeled with VIC (Applera Corporation, Norwalk, Conn.) and the target gene SAMS or YFP probe was labeled with FAM for the simultaneous detection of both fluorescent probes in the same duplex reactions. The primers and probes used in the qPCR analysis are listed below.

SAMS forward primer: SEQ ID NO:16
FAM labeled SAMS probe: SEQ ID NO:17
SAMS reverse primer: SEQ ID NO:18
YFP forward primer: SEQ ID NO:19
FAM labeled YFP probe: SEQ ID NO:20
YFP reverse primer: SEQ ID NO:21
HSP forward primer: SEQ ID NO:22
VIC labeled HSP probe: SEQ ID NO:23
HSP reverse primer: SEQ ID NO:24
FAM labeled DNA oligo probes and VIC labeled oligo probes were obtained from Applied Biosystems while the primers were obtained from MWG-Biotech AG (Bridgeport, Ga.).

Transgenic soybean events containing 1 or 2 copies of both the SAMS:ALS expression cassette and the LTP4:YFP expression cassette were selected for further gene expression evaluation and seed production (see Table 2). Events negative for YFP qPCR or with more than 2 copies for the SAMS or YFP qPCR were terminated. YFP expression detection in flowers as described in EXAMPLE 6 is also recorded in the same table.

TABLE 2

Relative transgene copy numbers and YFP expression of LTP4:YFP transgenic plants

| Event ID | YFP | YFP qPCR | SAMS qPCR |
|---|---|---|---|
| 5138.1.1 | + | 1.1 | 1.3 |
| 5138.4.1 | + | 7.5 | 5.2 |
| 5138.4.3 | + | 0.8 | 1.2 |
| 5138.4.4 | + | 0.8 | 1.1 |
| 5138.6.2 | + | 0.6 | 1.3 |
| 5138.6.3 | + | 0.5 | 0.9 |
| 5138.7.3 | + | 0.7 | 0.9 |
| 5138.7.4 | + | 0.7 | 1.0 |

Example 6

LTP4:YFP Expression in Stable Transgenic Soybean Plants

YFP gene expression was checked at different stages of transgenic plant development for yellow fluorescence emission under a Leica MZFLIII stereo microscope equipped with UV light source and appropriate light filters (Leica Microsystems Inc., Bannockburn, Ill.). No specific yellow fluorescence was detected during somatic embryo development or in vegetative tissues such as leaf, petiole, stem, or root of transgenic plant, or in very young flower bud when flower structure had not formed. Fluorescence was only detected in flower buds and flowers.

A soybean flower consists of five sepals, five petals including one standard large upper petal, two large side petals, and two small fused lower petals called kneel to enclose ten stamens and one pistil. The filaments of the ten stamens fuse together to form a sheath to enclose the pistil and separate into 10 branches only at the top to each bear an anther. The pistil consists of a stigma, a style, and an ovary in which there are normally 2-4 ovules that will eventually develop into seeds.

No fluorescence was detected in somatic embryos during tissue culture or vegetative tissues such as leaf, root, stem etc. of the LTP4:YFP transgenic plants. Specific fluorescence signal, white (greyscale display) or bright greenish yellow color (color display) was detected almost exclusively in the stigmas of flower bud, open flower, and young pods (FIG. 4). No fluorescence was detected in the sepals or petals of flower bud (FIG. 4A) or open flower (FIG. 4D). When the flower bud was opened (FIG. 4B), strong fluorescence was detected in the young stigma. No specific fluorescence was detected in the petals, developing anthers, filaments, style, or the ovary part of the pistil. The dull yellow color (white in grayscale display) in the developing anthers was non-specific similar to the dull yellow color from the petals (FIG. 4D). The same expression pattern continued to open flower stage though the non-specific yellow color in anthers became stronger (FIG. 4E). The stigma-specific fluorescence was better revealed in isolated developing pistil (FIG. 4C) and mature pistil (FIG. 4F). The exposed ovules as indicated by the white arrows (black arrows in grayscale display) did not show any fluorescence. The stigma remaining on R3 pod carried strong yellow fluorescence (FIG. 4G). The pollen grains attached to the stigma and style did not emit specific fluorescence. Yellow fluorescence could still be detected in the stigma remaining of even older R4 pod (FIG. 4H). The stigma remaining of pods older than the R4 pod would be dead and emit auto fluorescence under both YFP and CFP filters. Interestingly, fluorescence was detected in a restricted area of some young developing seeds in two of the total eight transgenic events (FIG. 4I).

In conclusion, the LTP4:YFP expression was highly specific to the stigmas of developing flowers and young pods. Limited expression in early developing seeds was also observed but in only two transgenic events, suggesting that the expression pattern was not universal. The biological significance of the highly specialized expression of the LTP4 gene in stigma, where pollination involving pollen-stigma interactions occurs, still needs to be explored in depth.

What is claimed is:

1. An isolated polynucleotide comprising
the sequence set forth in SEQ ID NO:1 or a full-length complement thereof,
wherein said isolated polynucleotide is a stigma-specific promoter.

2. A recombinant DNA construct comprising the isolated polynucleotide of claim 1 operably linked to at least one heterologous sequence.

3. The recombinant DNA construct of claim 2, wherein the heterologous sequence encodes a gene involved in anthocyanin biosynthesis, a gene involved in the synthesis of fragrant fatty acid derivatives, a gene that is determinative of flower morphology, a gene involved in biosynthesis of plant cytokinin or a gene involved in pollination compatibility.

4. The recombinant DNA construct of claim 3, wherein the gene involved in anthocyanin biosynthesis is dyhydroflavonol 4-reductase, flavonoid 3,5-hydroxylase, chalcone synthase, chalcone isomerase, flavonoid 3-hydroxylase, anthocyanin synthase, or UDP-glucose 3-O-flavonoid glucosyl transferase.

5. The recombinant DNA construct of claim 3, wherein the gene involved in the synthesis of fragrant fatty acid derivatives is S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthase, (E)-β-ocimene synthase, orcinol O-methyltransferase, or limonene synthase.

6. The recombinant DNA construct of claim 3, wherein the gene that is determinative of flower morphology is AGAMOUS, APETALA, or PISTILLATA.

7. The recombinant DNA construct of claim 3, wherein the gene involved in biosynthesis of plant cytokinin is isopentenyl transferase.

8. A vector comprising the recombinant DNA construct of claim 2.

9. A cell comprising the recombinant DNA construct of claim 2.

10. The cell of claim 9, wherein the cell is a plant cell.

11. A transgenic plant having stably incorporated into its genome the recombinant DNA construct of claim 2.

12. The transgenic plant of claim 11, wherein the plant is a flowering plant.

13. The transgenic plant of claim 12, wherein the flowering plant is rose, carnation, *Gerbera, Chrysanthemum*, tulip, *Gladioli, Alstroemeria, Anthurium*, lisianthus, larkspur, irises, orchid, snapdragon, African violet, or azalea.

14. A transgenic seed produced by the transgenic plant of claim 11.

15. A method of expressing a coding sequence or a functional RNA in a flowering plant comprising:
   a) introducing the recombinant DNA construct of claim 2 into the plant, wherein the at least one heterologous sequence comprises a coding sequence or a functional RNA;
   b) growing the plant of step a); and
   c) selecting a plant displaying expression of the coding sequence.

16. A method of transgenically altering a marketable flower trait of a flowering plant, comprising:
   a) introducing a recombinant DNA construct of claim 2 into the flowering plant;
   b) growing a fertile, mature flowering plant resulting from step a); and
   c) selecting a flowering plant expressing the at least one heterologous nucleotide sequence in flower tissue based on the altered marketable flower trait.

17. The method of claim 16 wherein the marketable flower trait is color, morphology, or fragrance.

\* \* \* \* \*